US012788251B2

(12) United States Patent
Ciriello et al.

(10) Patent No.: US 12,788,251 B2
(45) Date of Patent: Nov. 10, 2026

(54) OPTICAL COHERENCE TOMOGRAPHY COLOR MAPPING SYSTEM

(71) Applicant: Perceptive Technologies, Inc., Boston, MA (US)

(72) Inventors: Christopher John Ciriello, Boston, MA (US); Wei Kang, Newton Center, MA (US); Phillip Getto, Wellesley, MA (US); Angela Zhang, Stow, MA (US); Nhan Le, Southborough, MA (US); Victor Grinberg, Waltham, MA (US); Justin LaRue, Cambridge, MA (US)

(73) Assignee: Perceptive Technologies, Inc., Boston, MA (US)

( * ) Notice: Subject to any disclaimer, the term of this patent is extended or adjusted under 35 U.S.C. 154(b) by 0 days.

(21) Appl. No.: 19/294,262

(22) Filed: Aug. 7, 2025

(65) Prior Publication Data

US 2025/0359759 A1 Nov. 27, 2025

Related U.S. Application Data

(63) Continuation of application No. 19/048,848, filed on Feb. 7, 2025.

(60) Provisional application No. 63/551,052, filed on Feb. 7, 2024.

(51) Int. Cl.
*A61B 5/00* (2006.01)

(52) U.S. Cl.
CPC .......... *A61B 5/0066* (2013.01); *A61B 5/0088* (2013.01)

(58) Field of Classification Search
None
See application file for complete search history.

(56) References Cited

U.S. PATENT DOCUMENTS

2006/0187462 A1* 8/2006 Srinivasan ........... A61B 5/0066 356/479

FOREIGN PATENT DOCUMENTS

JP 2004347380 A * 12/2004
WO WO-2022212507 A1 * 10/2022 ........... A61B 5/0088

OTHER PUBLICATIONS

JP2004347380A—machine translation (Year: 2004).*

* cited by examiner

*Primary Examiner* — Serkan Akar
*Assistant Examiner* — Renee C Langhals
(74) *Attorney, Agent, or Firm* — George Jakobsche Patent Counsel PLLC

(57) ABSTRACT

An optical coherence tomography scanning system traverses its respective scan pattern quickly, typically completing an entire two-dimensional frame faster than a conventional raster scanner completes one raster line segment. To traverse the scan pattern quickly, the system takes fewer A-scans per length of scan pattern than a conventional OCT scanner. To compensate for the sparsity of the sample points along the respective scan line segments, and for gaps between respective line segments of the trajectory, the system acquires and combines several partially overlapping frames for each study to generate a dense OCT image. A visible light camera captures an image for each traversal of the scan pattern, but only a predetermined subset of pixels in the visible light image, which correspond to locations on the anatomical item interrogated by a sample arm of the OCT, are used to color corresponding pixels in the dense OCT image.

9 Claims, 20 Drawing Sheets

OPTICAL COHERENCE TOMOGRAPHY COLOR MAPPING SYSTEM

CROSS REFERENCE TO RELATED APPLICATIONS

This application claims a benefit of U.S. patent application Ser. No. 19/048,848, filed Feb. 7, 2025, titled "Optical Coherence Tomography Color Mapping System," the entire contents of which are hereby incorporated by reference herein, for all purposes.

BACKGROUND

Technical Field

The invention relates to optical coherence tomography, and more particularly to optical coherence tomography scanning systems that perform multiple fast, sparse scans to generate a dense image, and that map pixels captured by a separate camera onto the dense image.

Related Art

Dental caries is a common disease that affects more than 90% of American adults. Despite advances in preventive measures, dental caries continues to be a primary reason for invasive treatment to restore teeth. Over 35% of Americans do not see a dentist in any given year, and the United States Centers for Disease Control and Prevention (CDC) indicate that about 28% have untreated tooth decay. Of the patients that visit dentists, Pacific Dental Services (PDS) of Irvine, CA indicates that patient acceptance of an ideal dental treatment plan occurs only 28% of the time and states that the main reasons for this low acceptance rate are: cost of care, inconvenience of multiple and lengthy dental appointments, and poor case acceptance by both patients and insurance carriers.

Avoiding dentists for these reasons usually results in dental disease progression, periodontal disease, and other oral problems, e.g., lack of detection of oral cancers, which have been associated with numerous adverse medical impacts, including eating disorders, speech difficulties, poor social interactions, reduced employment potential, and an increased risk of systemic diseases, such as diabetes, cardiovascular disease, such as stroke and heart attacks, and Alzheimer's disease. Health issues resulting from poor oral health have been shown to culminate in over $45 B of lost productivity in the United States and over 34 M lost school hours for young adults. There is, therefore, a critical unmet need for affordable and efficient dental health care.

To address these problems and increase access to dental care, a means is needed to lower treatment costs, shorten appointments, and improve case acceptance by patients and insurers. Treatment costs can be lowered, and appointments can be shortened, by improving prevention and lower the costs of restorative intervention. Increased early and accurate diagnosis would improve preventative care. Automation of tooth preparation or restorative treatment would shorten dentist time and decrease associated costs and appointment times.

In early stages of dental caries, loss of minerals in a tooth can be reversed when there is a sufficient supply of calcium, phosphate, and fluoride ions in the mouth. These ions help to re-mineralize the tooth. Early and accurate diagnosis of dental caries lowers dental treatment costs, as it allows for the use of non-invasive treatment methods to prevent or forestall the onset and progression of the disease. Automation of dentist labor for restorative treatment via the use of robotics lowers treatment cost and shortens appointment times for dental disease that has progressed beyond the point of re-mineralization. However, such an approach requires an improved imaging modality that offers both true tooth geometry and high sensitivity and specificity, beyond the capabilities of radiographs, to guide robots. Neither dental radiographs nor cone-beam computed tomography (CBCT) is sufficiently accurate to replace intraoral scanners (IOS) for restorative dentistry. This is evidenced by the fact that dentists must use real-time visual and tactile feedback during tooth preparation to localize and remove all tooth decay.

To improve case acceptance by patients and insurers, a more sensitive and specific imaging modality that is easy to read by both patients and insurers is needed. Today, patients are unaccustomed to interpreting two-dimensional (2D) radiographs and thus are unable to independently verify the need for care without a provider's interpretation. Three-dimensional (3D) radiographs, such as CBCT, circumvent this problem, according to PDS, and improve overall case acceptance by 10%. Insurers rely on a variety of inputs to validate the need for care, including clinical notes and radiographs. However, radiographs have their own inherent limitations, including low sensitivity and specificity and an inability to image soft tissue and cracks in teeth. This low sensitivity and specificity of radiographs often creates discrepancies between providers and payers, resulting in patients not being covered by insurance, and discrepancies between providers, which lowers trust in the profession and, thus, case acceptance.

Optical coherence tomography (OCT) is an excellent imaging candidate technology as it offers several advantages over radiographs for dental applications. These advantages include fast 3D imaging, non-ionizing radiation, high dental sensitivity and specificity, and high spatial resolution (currently about 1-20 km). However, OCT has limitations that restrict its use in dentistry, such as limited penetration depth, a small field of view (FOV) that prevents full arch imaging, a long capture time that can cause motion distortion within a single volume, and a need for complex registration to achieve surface trueness required of an intraoral scanner (IOS) or to guide automated tooth preparation surgery.

SUMMARY OF EMBODIMENTS

According to a first aspect of the present disclosure there is provided an optical coherence tomography (OCT) system for scanning an anatomical item, the system comprising: a scanning device, which is moveable by a user relative to the anatomical item to scan the anatomical item.

The scanning device comprises: a beam steering system, which is operable to deflect a sample beam by respective, selected amounts in two directions; one or more optical elements, which direct the sample beam through an imaging window of the scanning device to an exterior of the scanning device, and which receive light returned from the anatomical item through the imaging window and direct said returned light to an interferometry system of the OCT system, wherein the interferometry system is configured to cause interference between the returned light and light from a light source that produces the sample beam, and to analyze said interference; and a camera, operable to capture visible light images of a region exterior the scanning device, adjacent the imaging window, each of said images comprising a plurality of pixels, the camera having an optical axis that defines an acute angle with respect to a central axis for the sample beam, following emission through the imaging window.

The system further comprises: at least one processor; and data storage, on which is stored instructions that, when executed by the at least one processor, cause the OCT system to perform actions comprising:

Controlling the beam steering system such that the sample beam, after exiting the imaging window, repeatedly traverses a two-dimensional scanning pattern, with the movement of the scanning device by the user relative to the anatomical item causing the repeated traversals of the scanning pattern to be applied to respective, different locations on the anatomical item;

For each traversal of the scanning pattern, carrying out a plurality of A-scans at respective points distributed over the scanning pattern, so as to generate a set of volumetric OCT scanning data, said repeated traversals of the scanning pattern thereby generating a plurality of sets of volumetric OCT scanning data;

During said repeated traversals of the scanning pattern, controlling the camera to repeatedly capture visible light images of the anatomical item;

For each set of volumetric OCT scanning data:

Identifying a plurality of points on an exterior surface of the anatomical item, each of the plurality of points corresponding to one the plurality of A-scans used to generate the set of volumetric OCT scanning data;

Determining an association between each of said plurality of points and a respective subset of pixels of an image captured by the camera at a time corresponding to the volumetric OCT scanning data; and Determining spacings between the subsets of pixels corresponding to the plurality of points;

Based on said spacings, identifying, within the subsets of pixels, groups of potentially mutually obscuring subsets of pixels, each group of potentially mutually obscuring subsets of pixels corresponding to a group of potentially mutually obscuring exterior surface points among the plurality of points; and Generating a 3D model of the anatomical item, using the plurality of sets of volumetric OCT scanning data, wherein the generating of the 3D model comprises:

For each set of volumetric OCT scanning data, adding a plurality of exterior surface portions, each of which is based on at least one of the plurality of points on the exterior surface of the anatomical item identified using the set of volumetric OCT scanning data; and Determining coloring parameters for the plurality of exterior surface portions, based on said association between each of said plurality of points and the respective subset of pixels of said image captured by the camera. For a given exterior surface portion that is based on a given point of a group of potentially mutually obscuring points, the determining of the color parameters is further based on a proximity of the given point to the camera, relative to the proximity to the camera of each of the other potentially mutually obscuring exterior surface points in the group.

In some examples, for said given exterior surface portion based on the given point of the group of potentially mutually obscuring points, the determining of the color parameters comprises determining whether the given point is closer to the camera than all other potentially mutually obscuring exterior surface points in the group, and, only if so, the determining of the color parameters of the given exterior surface portion is based on the subset of pixels corresponding to the given point.

In some examples, if the given point is not closer to the camera than all other potentially mutually obscuring exterior surface points in the group, the determining of the color parameters of the given exterior surface portion is based on at least one predetermined contrast color.

In some examples, said identifying, within the subsets of pixels, groups of potentially mutually obscuring subsets of pixels, is further based on respective distances from the camera of the points corresponding to the subsets of pixels.

According to a further aspect of the present disclosure there is provided an optical coherence tomography (OCT) system for scanning an anatomical item, the system comprising: a scanning device, which is moveable by a user relative to the anatomical item to scan the anatomical item.

The scanning device comprises: a beam steering system, which is operable to deflect a sample beam by respective, selected amounts in two directions; one or more optical elements, which direct the sample beam through an imaging window of the scanning device to an exterior of the scanning device, and which receive light returned from the anatomical item through the imaging window and direct said returned light to an interferometry system of the OCT system, wherein the interferometry system is configured to cause interference between the returned light and light from a light source that produces the sample beam, and to analyze said interference; and a camera, operable to capture visible light images of a region exterior the scanning device, adjacent the imaging window, wherein the camera and the window are disposed at a distal end of the scanning device, with an optical axis of the camera being oriented towards said region exterior the scanning device.

The system further comprises: at least one processor; and data storage, on which is stored instructions that, when executed by the at least one processor, cause the OCT system to perform actions comprising:

Controlling the beam steering system such that the sample beam, after exiting the imaging window, repeatedly traverses a two-dimensional scanning pattern, with the movement of the scanning device by the user relative to the anatomical item causing the repeated traversals of the scanning pattern to be applied to respective, different locations on the anatomical item;

For each traversal of the scanning pattern, carrying out a plurality of A-scans at respective points distributed over the scanning pattern, so as to generate a set of volumetric OCT scanning data, said repeated traversals of the scanning pattern thereby generating a plurality of sets of volumetric OCT scanning data;

During said repeated traversals of the scanning pattern, controlling the camera to repeatedly capture visible light images of the anatomical item;

For each set of volumetric OCT scanning data:

Identifying a plurality of points on an exterior surface of the anatomical item, each of the plurality of points corresponding to one the plurality of A-scans used to generate the set of volumetric OCT scanning data; and Determining an association between said plurality of points and pixels of an image captured by the camera at a time corresponding to the volumetric OCT scanning data; and Generating a 3D model of the anatomical item, using the plurality of sets of volumetric OCT scanning data, wherein the generating of the 3D model comprises:

For each set of volumetric OCT scanning data, adding a plurality of exterior surface portions, based on the plurality of points on the exterior surface of the anatomical item identified using the set of volumetric OCT scanning data; and Determining coloring parameters for the plurality of exterior surface portions, based on said pixels of the image captured by the camera at the time corresponding to the volumetric OCT scanning data.

In some examples, for each set of volumetric OCT scanning data, each of the plurality of points on the exterior surface of the anatomical item corresponds to one the plurality of A-scans used to generate the set of volumetric OCT scanning data. For each set of volumetric OCT scanning data, determining the association between said plurality of points and said pixels of the image captured by the camera at the time corresponding to the volumetric OCT scanning data comprises determining an association between each of said plurality of points and a respective subset of the pixels of the image captured by the camera at the time corresponding to the volumetric OCT scanning data. For each set of volumetric OCT scanning data, each of the corresponding exterior surface portions is based on at least one of the plurality of points on the exterior surface of the anatomical item identified using the set of volumetric OCT scanning data. The determining of the coloring parameters for the plurality of exterior surface portions is based on said association between each of said plurality of points and the respective subset of pixels of said image captured by the camera.

In some examples, the optical axis of the camera extends through the window.

In some examples, the camera and the window are disposed on a first lateral side of the scanning device.

In some examples, the window is disposed on a first lateral side of the scanning device and the camera is disposed on an opposing, second lateral side of the scanning device. In a specific example, the one or more optical elements comprise a distal mirror, which directs the sample beam in a direction generally perpendicular to a length of the scanning device, through the window, and wherein the camera is disposed proximally of the distal mirror.

In some examples, the has an optical axis that defines an acute angle with respect to a central axis for the sample beam, following emission through the imaging window.

Optionally, in any of the aspects disclosed herein, the scanning device is a handheld device.

According to a further aspect, the present disclosure provides an optical coherence tomography (OCT) system for scanning an anatomical item The system comprises: a scanning device, which is moveable by a user relative to the anatomical item to scan the anatomical item, the scanning device comprising: a beam steering system, which is operable to deflect a sample beam by respective, selected amounts in two directions; one or more optical elements, which direct the sample beam through an imaging window of the scanning device to an exterior of the scanning device, and which receive light returned from the anatomical item through the imaging window and direct said returned light to an interferometry system of the OCT system, wherein the interferometry system is configured to cause interference between the returned light and light from a light source that produces the sample beam, and to analyze said interference; and a camera, operable to capture visible light images of a region exterior the scanning device, adjacent the imaging window, each of said images comprising a plurality of pixels; at least one processor; and data storage, on which is stored instructions that, when executed by the at least one processor, cause the OCT system to perform various actions.

The actions comprise: controlling the beam steering system such that the sample beam, after exiting the imaging window, repeatedly traverses a two-dimensional scanning pattern, with the movement of the scanning device by the user relative to the anatomical item causing the repeated traversals of the scanning pattern to be applied to respective, different locations on the anatomical item; for each traversal of the scanning pattern, carrying out a plurality of A-scans at respective points distributed over the scanning pattern, so as to generate a set of volumetric OCT scanning data, said repeated traversals of the scanning pattern thereby generating a plurality of sets of volumetric OCT scanning data; and during said repeated traversals of the scanning pattern, controlling the camera to repeatedly capture visible light images of the anatomical item.

The actions further comprise, for each set of volumetric OCT scanning data: identifying a plurality of points on an exterior surface of the anatomical item, each of the plurality of points corresponding to one the plurality of A-scans used to generate the set of volumetric OCT scanning data; and determining an association between each of said plurality of points and a respective subset of pixels of an image captured by the camera at a time corresponding to the volumetric OCT scanning data.

The actions further comprise: generating a 3D model of the anatomical item, using the plurality of sets of volumetric OCT scanning data. The generating of the 3D model comprises: for each set of volumetric OCT scanning data, adding a plurality of exterior surface portions, each of which is based on at least one of the plurality of points on the exterior surface of the anatomical item identified using the set of volumetric OCT scanning data; and determining coloring parameters for the plurality of exterior surface portions, based on said association between each of said plurality of points and the respective subset of pixels of said image captured by the camera.

In some examples, the determining of coloring parameters for each of the plurality of exterior surface portions may be based on the subset(s) of pixels associated with the at least one of the plurality of points on the exterior surface of the anatomical item that was used to generate the exterior surface portion in question.

In some examples, the generating of the 3D model can, for example, be carried out in real-time, as each set of OCT data is generated. In addition, or instead, the generating can be carried out iteratively, so that successive pluralities of exterior surface portions are added and the color parameters therefor are generated, in turn.

In some examples, the associating of each of said plurality of points on the exterior surface of the anatomical item with the respective subset of the pixels of the corresponding image is based on calibration data, which define a correspondence between each of the plurality of A-scans in the scanning pattern and a subset of pixels of the camera.

In some examples, the associating of each of said plurality of points on the exterior surface of the anatomical item with the respective subset of the pixels of the corresponding image is based on a distance of the point in question from the scanning device.

In some examples, an optical axis of the camera is offset and/or angled with respect to an optical axis of the sample beam, when the sample beam is undeflected by the beam steering system.

In some examples, the scanning device is a handheld device. In other examples, the scanning device is, for instance, moved by a robotic arm (and may, therefore, be connected to a distal end thereof).

In a further aspect, the present disclosure provides a tomography system. The tomography system includes a probe housing, an optical coherence tomography system, a visible light camera, a moveable mirror system, a motor, and a controller.

The probe housing defines a window. The probe housing is configured to be oriented and reoriented, and moved along a path proximate an anatomical item in a live patient. The anatomical item has a surface.

The optical coherence tomography system includes an optical detector and a light source. The light source is configured to produce a sample arm. During operation, a portion of the sample arm extends outside the probe housing, in free space, via the window, in a direction that depends on orientation and position of the probe housing.

The visible light camera has a field of view in the direction of the sample arm.

The moveable mirror system is disposed within the probe housing. The moveable mirror system is configured to redirect the sample arm.

The motor is disposed within the probe housing and is coupled to the mirror system.

The controller is configured to automatically drive the motor to repeatedly alter orientation of the mirror system about two different axes to thereby repeatedly scan the surface of the anatomic item with light of the sample arm along a trajectory according to a deterministic two-dimensional scan pattern. Each traversal of the scan pattern defines a respective two-dimensional scan area on a respective portion of the surface of the anatomic item, thereby collectively defining a plurality of scan areas. Each traversal of the scan pattern yields a respective sparse OCT data frame having a respective first pixel density captured from within the respective two-dimensional scan area, while the probe housing was at a respective orientation and position.

For each traversal of the scan patter, the visible light camera captures a dense visible data frame. Thus, repeated scans of the surface of the anatomic item collectively yield a plurality of sparse OCT data frames and a plurality of dense visible data frames, as the probe housing is oriented, reoriented, and moved along the path.

The controller is configured to automatically receive pixel data from the optical detector for the plurality of sparse OCT data frames and pixel data from the visible light camera for the plurality of dense visible data frames. At least some frames of the plurality of sparse OCT data frames are captured from different respective probe housing orientations and/or positions. At least some frame pairs of the plurality of sparse OCT data frames have partially overlapping respective scan areas.

For each dense visible data frame, the controller is configured to automatically extract only a predetermined subset of pixels of the dense visible data frame that corresponds to locations on the anatomical item interrogated by the sample arm.

The controller is configured to automatically generate a dense image data frame by combining pixel data of at least partially overlapping frames of the plurality of sparse OCT data frames. The controller is configured to automatically color pixels of the dense image data frame according to corresponding pixels of the subset of pixels. The dense data frame has a second pixel density greater than the first pixel density.

Optionally, in any embodiment, the controller is configured to color the pixels of the dense image data frame that represent a surface of the anatomical item.

Optionally, in any embodiment, the predetermined subset of pixels of the dense visible data frame consists of pixels that were identified in a calibration process.

Another embodiment of the present invention provides a method for predetermining a subset of pixels of a dense visible data frame. The method includes scanning a reflective target with the OCT system, imaging the target with a pixelated digital camera to generate a dense image, and identifying a plurality of pixels in the dense image. Each such pixel has a brightness value greater than a predetermined value. The plurality of pixels corresponds to only locations on the target illuminated by the OCT system.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Figure 1:
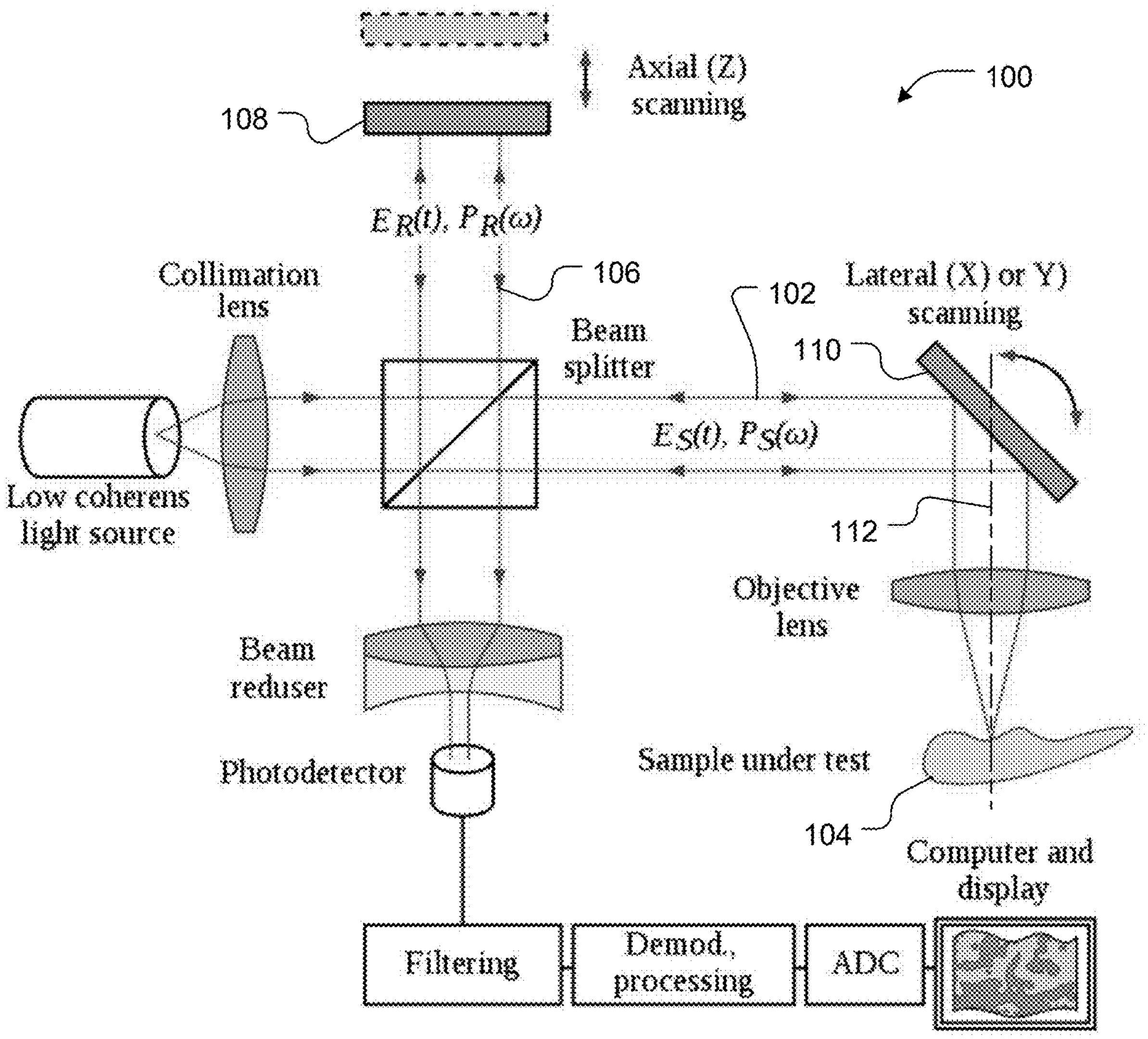
(Prior Art) Fig. 1
FIG. 1 is a schematic block of an optical coherence tomography system, according to the prior art.

Embodiments of the present invention solve problems associated with prior art OCT scanning technology. To avoid unacceptable amounts of motion blur, these embodiments traverse their respective scan patterns quickly, typically completing an entire frame faster than a conventional raster scanner completes one raster line segment. To traverse their scan patterns quickly, these embodiments take fewer A-scans per length of scan pattern than conventional OCT scanners. Each traversal of the scan pattern covers a 2D area, not merely a 1D straight line, of the scanner's field of view. The 2D area field of view area of each traversal of the scan pattern at least partially overlaps the 2D area field of view area of another traversal of the scan pattern.

As a result, each traversal of the scan pattern (frame) interrogates only a relatively small portion of the field of view of the scanner and leaves relatively large portions ("gaps," exemplified by gaps 934 and 936 in FIG. 9) of the scanner's field of view uninterrogated. That is, each traversal of the scan pattern traces a pattern on a surface of an interrogated object. The scan pattern, as viewed on the object's surface, is made up of some combination of curved lines, straight lines, loops, Lissajous figures, and the like, along which A-scans are taken. The scan pattern typically consists of a single continuous curved line traced on the object surface. Thus, each frame is typically not rectangular, and pixels of the frame are not necessarily regularly spaced on the object surface. As viewed on the object surface, these lines, loops, etc. of a given frame define areas (the "gaps") that are not covered by any line in that frame and are not, therefore, interrogated during the frame.

To compensate for the sparsity of the sample points along their respective scan patterns, and for the gaps between respective line segments of the trajectory, these embodiments acquire and combine several partially overlapping frames for each study. For example, a boundary between air and the surface of the interrogated object may be automatically extracted for each A-scan by processing the A-scan to locate a largest change in reflectivity, which yields a 3D surface for each traversal of the scan pattern, i.e., each sparse OCT frame. A plurality of sparse OCT frames are then registered together, matching surface features of partially overlapping sparse OCT frames The embodiments rely on movement of a scanner between frames, such as movement of a hand-held probe along a path. In the prior art, such movement would cause motion blur. However, due to the speed with which each frame is captured (preferably at least about 50 or 100 frames per second) in these embodiments, each frame suffers no or negligible motion blur. Instead, due to the motion of the scanner, each frame captures an image of the scanned object from a slightly different viewpoint. Consequently, as viewed on the surface of the scanned object, the scan patterns of successive frames tend to interlace, such that gaps left unscanned in one frame are at least partially scanned in other frames. Eventually, the object is traversed by a relatively large number of traversals of the scan pattern, many or each of which is taken from a different viewpoint. An exemplary embodiment generates (synthesizes) a dense image by combining pixel or voxel data from the various sparse frames. OCT systems that generate a dense image by combining pixel or voxel data from various sparse OCT frames are described in Applicant's earlier PCT publication, WO2024/054937A1, the disclosure of which is incorporated herein in its entirety.

OCT images reveal subsurface details, such as differences in reflectivity that may indicate differences in materials or densities. However, such 3D images are difficult to analyze by users who are untrained and inexperienced. Thus, most dental patients, and some practitioners, are unable to analyze OCT images. Augmenting an OCT image with realistic colors of surfaces would make the images much easier to understand and analyze. Embodiments of the present disclosure capture humanly visible image data simultaneously with OCT data and augment the OCT image data by coloring pixels that represent surfaces.

Color Mapping

Some prior art systems color the data captured by one imaging device using color data captured by another imaging device. For example, a hypothetical prior art device may simultaneously capture dense OCT data and dense visible image data and register the visible data over the OCT data. See, for example, U.S. Pat. No. 11,839,448 ("Intraoral OCT with Color Texture") and U.S. Pat. No. 11,382,517 ("Intra-Oral Scanning Device with Integrated Optical Coherence Tomography (OCT)," the entire contents of each of which are hereby incorporated by reference herein, for all purposes. However, prior art coloring (also sometimes referred to as "texturing") schemes involve pairs of imaging devices that both capture dense rectangular image frames with at least approximately equal fields of view. That is, each image frame has a pixel density at least approximately equal to a final image's pixel density, and each visible image frame provides sufficient pixels to cover a corresponding OCT frame. In particular, a single visible image frame provides a sufficient number of pixels, and a sufficient pixel density, to yield an image that is understandable by a human user.

In contrast, in embodiments of the present disclosure, each OCT volumetric frame is sparse, because it is produced by a sparse scanning pattern. For example, the scanning pattern may include substantial gaps between different linear portions thereof (e.g., gaps that are significantly larger than the gap between successive a-scans), leaving gaps of uninterrogated object, as summarized above. This sparsity of the scanning pattern allows each OCT frame to be captured very quickly. On the other hand, such a sparse volumetric frame provides an insufficient number of pixels or voxels to register with a dense rectangular visual image, because most of the pixels in the rectangular visual image would not have corresponding pixels or voxels in the OCT image. Hence, conventional techniques for registering visual image data with OCT data cannot be applied.

Embodiments of the present disclosure solve this problem by using only visual image pixels of each rectangular visual frame that correspond to OCT pixels or voxels captured at the same time. In other words, although a conventional pixelated visible image camera can be used to capture the visual image, the system uses only pixels that correspond to locations in the field of view that are interrogated (illuminated) by the OCT system. As the embodiments build up a dense 3D model of the object by combining OCT pixels or voxels from many sparse volumetric OCT frames, they also build up many sets of sparse image data that can be used to color/texture the surface of the dense 3D model.

Figure 13:
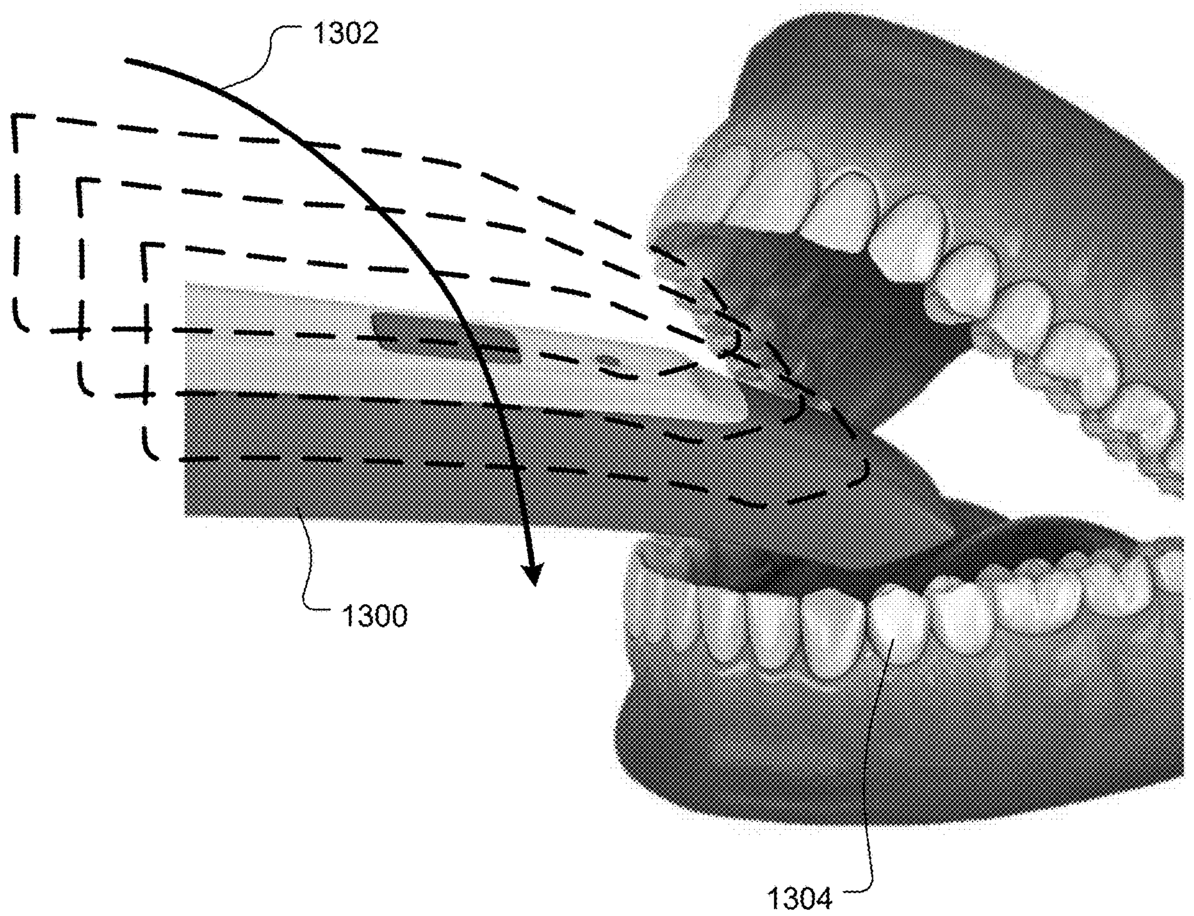
FIG. 13 illustrates use of an embodiment of the present invention and, in particular, translating a scanning wand in space along a path proximate an anatomical item under test.
Figure 14:
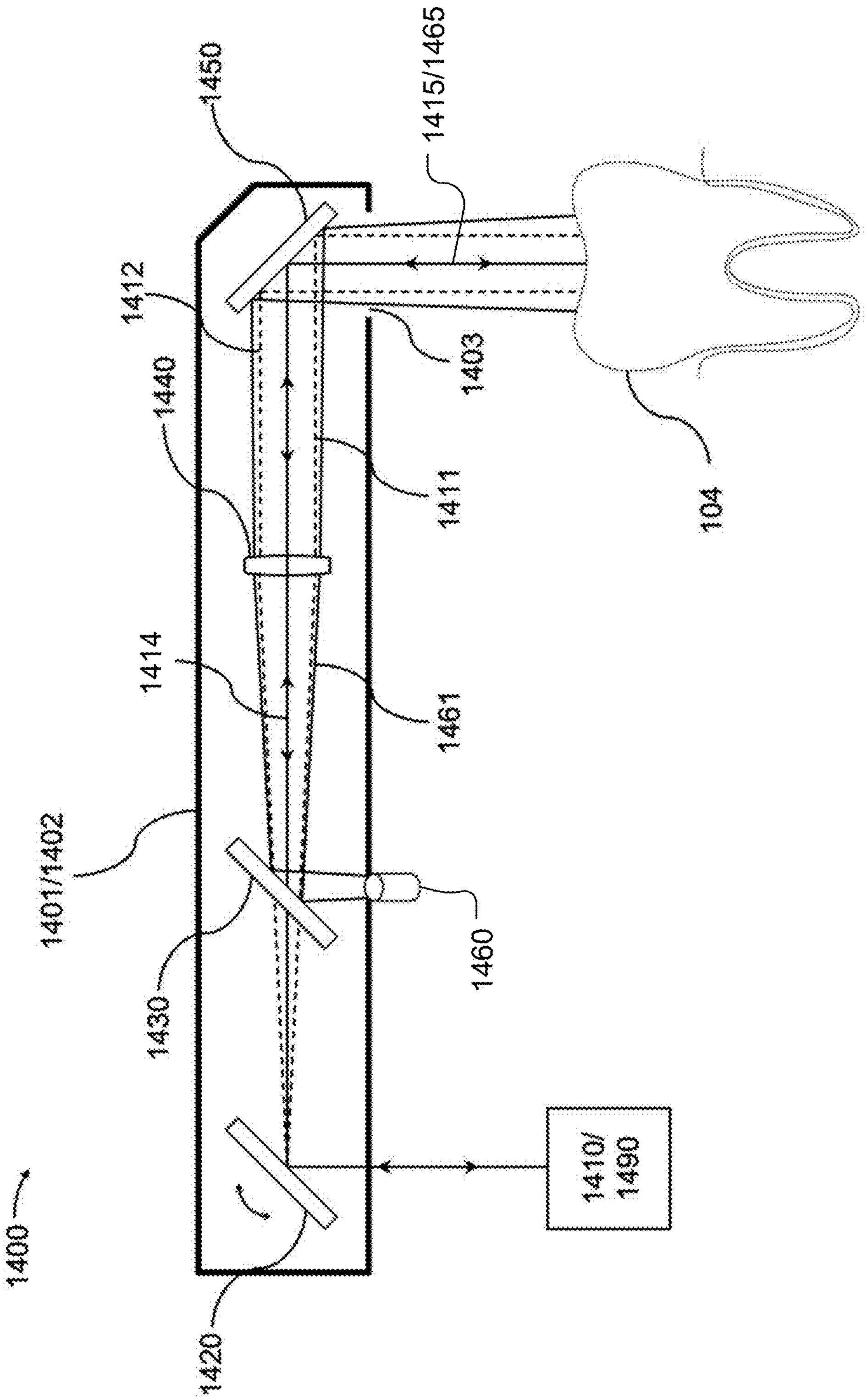
FIG. 14 is a partially schematic block diagram of an OCT color mapping system, according to an embodiment of the present disclosure.

FIG. 14 is a schematic diagram of an OCT color mapping system 1400, according to an embodiment of the present disclosure. As shown, the system 1400 comprises a scanning device 1401 that is moveable by a user (e.g., as shown in FIG. 13). As also shown, the scanning device 1401 comprises a beam steering subsystem 1420, which is operable to deflect a sample beam 1414 by respective, selected amounts in two directions. This enables the sample beam 1414 to be steered such that it traverses a 2D scanning pattern. As shown in FIG. 14, the beam steering subsystem 1420, and various optical elements 1430, 1440, 1450 are contained within a housing 1402 of the scanning device 1401. This may reduce the risk of contamination of such optical components.

In the particular example shown in FIG. 14, the beam steering subsystem 1420 comprises a moveable mirror that can be driven by a motor (such as a MEMS actuator) to tilt/rotate in two independent directions. However, this is by no means essential and in other examples the beam steering subsystem 1420 could comprise two (or perhaps more) mirrors, each of which can be driven by a motor in only one direction, or, more broadly, could comprise motor-driven lenses or prisms, or deformable lenses or prisms.

As further shown in FIG. 14, the sample beam 1414 is produced by a light source 1410 (such as a near infra-red light source), which, in the particular embodiment shown, does not form part of the scanning device 1401, but is instead comprised by a separate module (such as a cart), that also comprises an interferometry system 1490 of the OCT system 1400. The OCT system 1400 may comprise an optical fiber that conveys the light for the sample beam 1414 from the light source 1410 to the scanning device 1401, while still enabling the scanning device 1401 to move relative to the module that provides the light source 1410 and interferometry system 1490.

FIG. 14 shows how the sample beam 1414, after interacting with the beam steering subsystem 1420, passes through a dichroic mirror 1430, which is configured such that it transmits/does not reflect the wavelength(s) of light of the sample beam 1414. The sample beam 1414 then interacts with a focusing lens 1440. In the particular example shown, the focusing lens 1440 is configured as a telecentric lens for the various potential deflections of the sample beam 1414, so that, the sample beam 1414 is always parallel to the optical axis after passing through the focusing lens 1440 regardless of the deflection imparted by the steering system 1420. Hence, as shown, the focusing lens 1440 causes the sample beam 1414 to be parallel to the optical axis when deflected to a maximum extent in one sense, as indicated by dashed line 1411, and when deflected to a maximum extent in the opposite sense, as indicated by dashed line 1412. Having been made parallel to the optical axis, the sample beam 1414 is then deflected by a distal mirror 1450, which redirects the sample beam 1414 (for example in a substantially perpendicular direction) through a window 1403 of the scanning device 1401, towards an object 104 being scanned, which, in the example shown, is a tooth 104. Though not shown in FIG. 14, the window 1403 may suitably comprise a transparent element to protect the optical elements from contamination.

As will be appreciated, an amount of the light applied by the sample beam 1414 to the object 104 being scanned will be reflected and/or backscattered by the object 104 and will return through the window 1403. The same optical elements that transmitted the sample beam 1414 to the object 104 transmit such returned light back through the scanning device 1401, to the interferometry system 1490.

As will be understood, the interferometry system 1490 is configured to cause interference between the sample beam 1414 and the light coming directly from the light source 1410, and to analyze such interference. Consequently, the interferometry system 1490 may include a mirror (or other reflector), as part of a “reference arm”, along which light coming directly from the light source 1410 is transmitted, before it interferes with the light returned from the object, which is transmitted along a “sample arm”. As will also be understood, the interferometry system 1490 will typically include a photodetector to analyze the interference between the reference and sample arms, as is explained below with reference to FIG. 1.

Returning to FIG. 14, it will be noted that the scanning device 1401 further comprises a camera 1460, which is operable to capture visible light images of a region exterior the scanning device, adjacent the window 1403. The camera 1460 can, for example, be a pixelated digital camera that yields a rectangular pixelated image. In the particular example shown in FIG. 14, visible light from the object 104 passes through the same window 1403 as the sample beam 1414 and is diverted towards the camera 1460 by the dichroic mirror 1430. However, as will be explained below with reference to FIGS. 15A and 15B, such an arrangement is by no means essential.

To improve the quality of the visible light images captured by the camera 1460 (or otherwise), the OCT system 1400 may further comprise a visible light source (not shown) to illuminate the object 104 being scanned. Such a visible light source can, for example, be mounted at a distal end of the scanning device 1401, adjacent to the window 1403.

As will be described in further detail below, sparse visible light pixel data is obtained from the camera 1408 and is combined with sparse OCT frame data, in order to build a dense, textured/colored 3D model of the object 104 being scanned.

It should be appreciated that the particular configuration/arrangement of optical elements shown in FIG. 14 is by no means essential and that various other kinds of optical elements, such as lenses, prisms, mirrors etc., could be used instead, in various alternative arrangements, in order to direct the sample beam 1414 through the window 1403 and to receive and return light reflected from the object 104 to the interferometry system. In particular, while the use of a telecentric lens may, for example, make analysis of the OCT data and/or calibration of the system 1400 somewhat simpler, it is by no means essential. Furthermore, it is by no means essential that the camera 1408 receives light through the same window 1403 used for OCT. In this regard, reference is directed to FIG. 15A, which is a schematic diagram of a further example of an OCT color mapping system 1500.

Figure 15A:
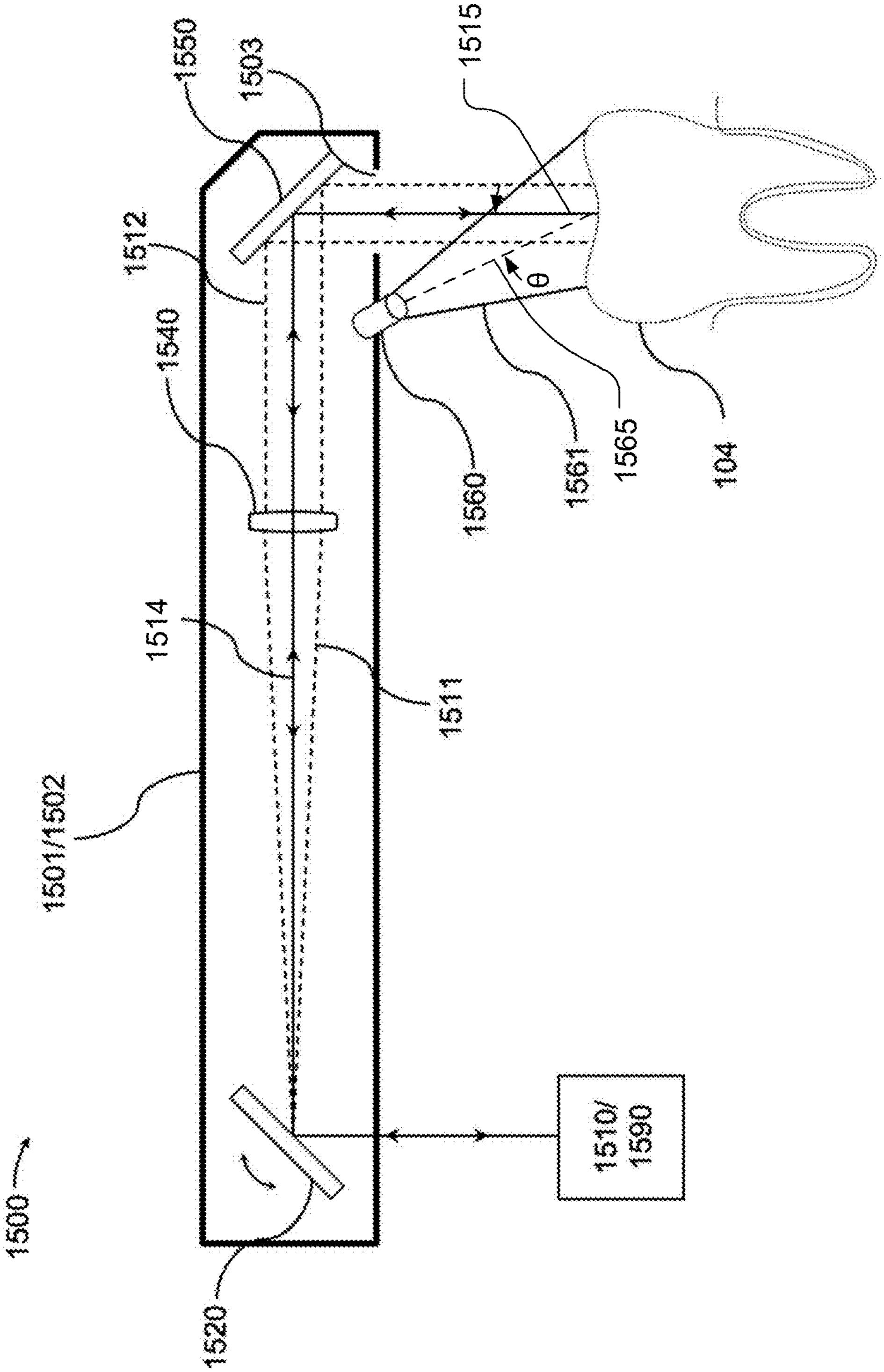
FIG. 15A is a partially schematic block diagram of an OCT color mapping system, according to another embodiment of the present disclosure.

The OCT system 1500 of FIG. 15A includes many of the same elements as the OCT system 1400 of FIG. 14. Accordingly, like reference numerals are used for the same features, but with an offset of 100.

As shown, in the OCT system 1500 of FIG. 15A, the camera 1560 is mounted at the distal end of the scanning device 1501, adjacent to the window 1503 used to receive backscattered light for OCT. Furthermore, it will be noted that the optical axis 1565 of the camera 1560 is offset from, and angled with respect to, the central axis 1515 of the sample beam 1514, following its emission through the window 1503. The angle, θ, that is defined between the optical axis 1565 of the camera 1560 and the central axis 1515 of the sample beam 1514, following its emission through the window 1503, is shown clearly in FIG. 15A. However, the field of view of the camera 1560 is nevertheless arranged such that it can capture images of a region adjacent to the window 1503. Moreover, the camera may be arranged such that an object 104 is centrally in the camera's field of view 1561 when the object is located at an optimal distance for OCT scanning.

Figure 15B:
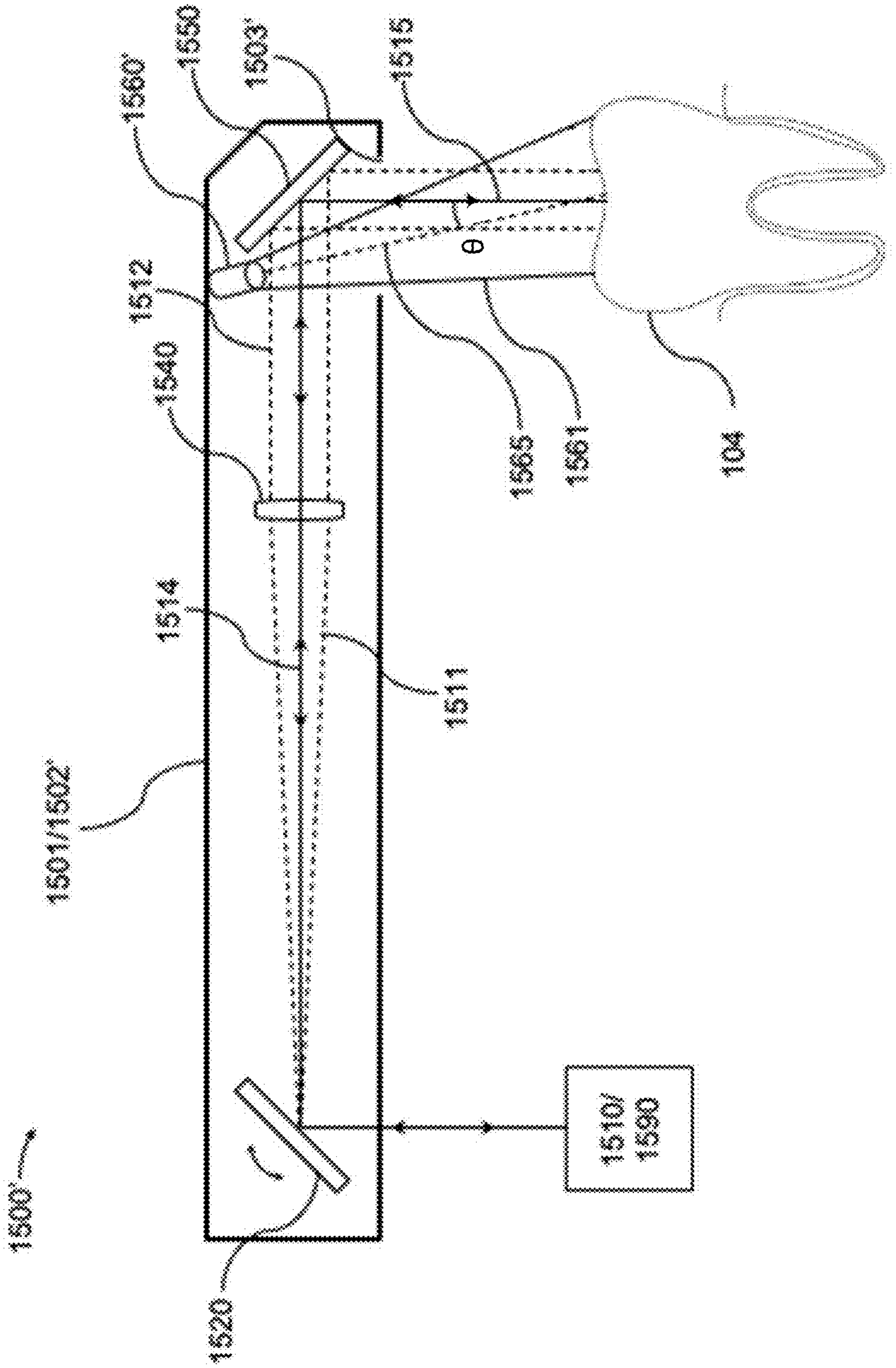
FIG. 15B is a partially schematic block diagram of a modified version of the OCT color mapping system of FIG. 15A

FIG. 15B is a schematic diagram of a still further example of an OCT color mapping system 1500'. The OCT color mapping system 1500' of FIG. 15B is substantially the same as the OCT color mapping system 1500 of FIG. 15A, except for the arrangement of the camera 1560' and the window 1503'.

More particularly, whereas the camera 1560 in the OCT color mapping system 1500 of FIG. 15A is disposed on the same lateral side of the scanning device 1501 as the window 1503, the camera 1560' of the OCT color mapping system 1500' of FIG. 15B is disposed on the opposite lateral side of the scanning device 1501' to the window 1503', and contained within the housing 1502' of the scanning device 1501'. Furthermore, in the particular example shown, the camera 1560' is located proximally of the distal mirror 1550 of the scanning device 1501'; however, while such an arrangement may be relatively compact, the camera 1560' could, in other examples, be located distally of the distal mirror 1550, but still contained within the housing 1502' of the scanning device 1501'.

Moreover, in the OCT color mapping system 1500' of FIG. 15B, the camera 1560' utilizes the window 1503' for capturing images; put differently, its optical axis 1565 extends through the window 1503'. Hence (or otherwise), window 1503' is used for capturing both visible light images (using the camera 1560') and OCT volumetric images. By contrast, the camera 1560 in the OCT color mapping system 1500 of FIG. 15A does not utilize the window 1503 for capturing images (though, in a modified version, for example where the window 1503 was suitably enlarged, it could do so).

As discussed earlier, the OCT systems 1400, 1500 are configured such that they can build up a dense 3D model of the object 104 by combining OCT pixels or voxels from many sparse volumetric OCT frames, and can texture/color the dense 3D model using many sets of sparse image data collected simultaneously with the volumetric OCT frames. To assist in doing so, a correlation of the pixels of the visible light camera 1460 with A-scans carried out by the OCT system (and, in consequence, voxels or pixels of each OCT frame) can be established by a calibration process. To establish which pixels of the visible light camera 1460 correspond to particular A-scans carried out by the OCT system, a calibration object having a surface that is photoluminescent (e.g., phosphorescent) or highly reflective is placed before the system, preferably perpendicular to the central axis 1415 of the sample beam 1414, in place of the object 104. The OCT system scans the surface along the scan pattern with relatively high intensity NIR light, and the visible light camera 1460 detects points/spots on the surface of the calibration object that are illuminated by the NIR light, each of which corresponds to a respective A-scan.

It should also be appreciated that, in OCT systems where the light source for OCT imaging is a swept-source capable of producing NIR and visible light, calibration can also/instead be carried out by causing the OCT light source to emit visible light towards a calibration object, and then imaging the resultant visible light spots on the calibration object, using the visible light camera 1460.

Figure 16:
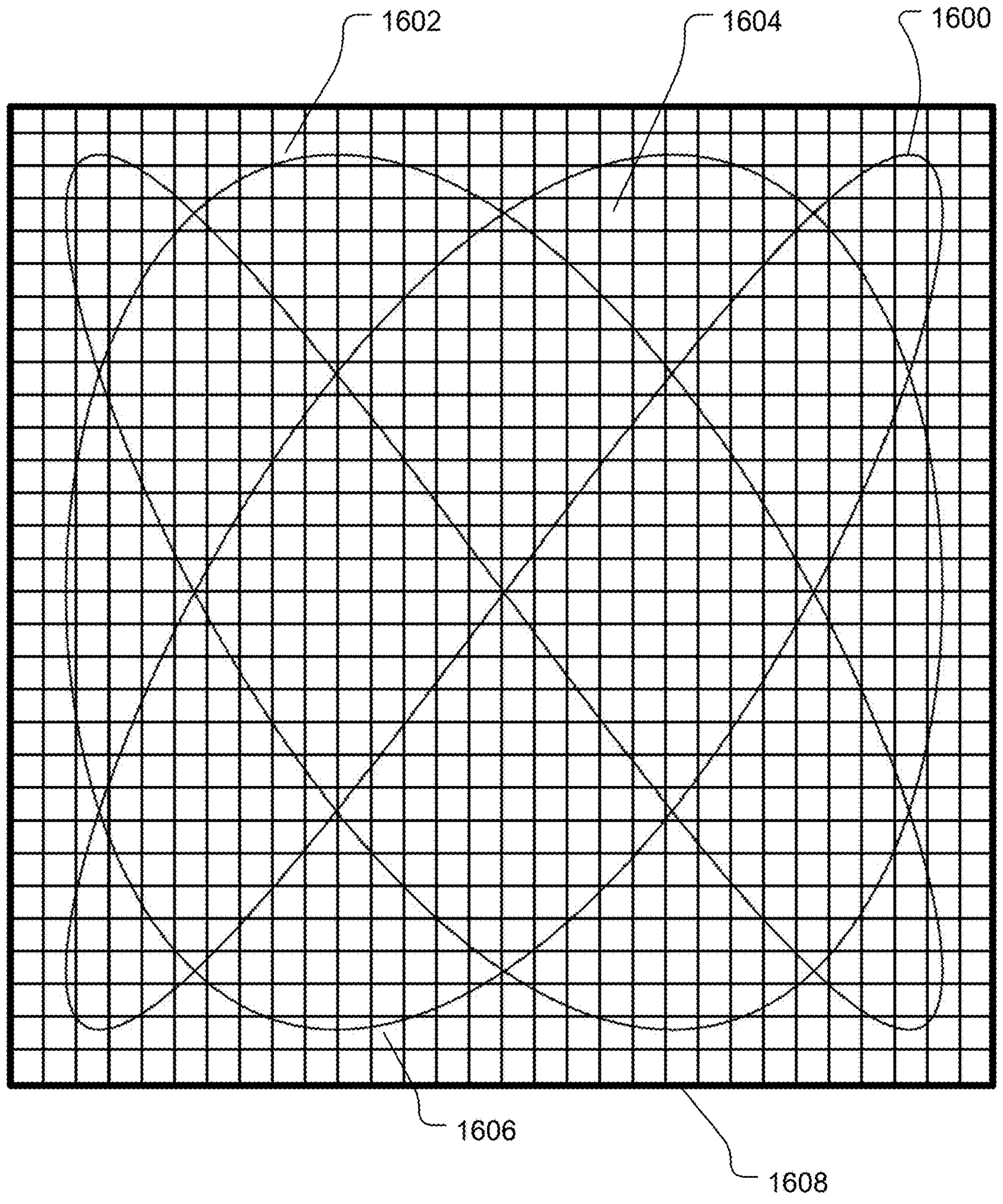
FIG. 16 illustrates an exemplary hypothetical scan pattern, as imaged by an exemplary hypothetical visible light camera of the OCT color mapping system of FIG. 14, according to an embodiment of the present disclosure.

FIG. 16 illustrates an exemplary hypothetical scan pattern 1600 (here, a Lissajous figure), as imaged by an exemplary hypothetical visible light camera. Pixels of the visible light camera are shown as squares, exemplified by squares 1602, 1604, and 1606, and the visible light camera frame is indicated at 1608.

Figure 17:
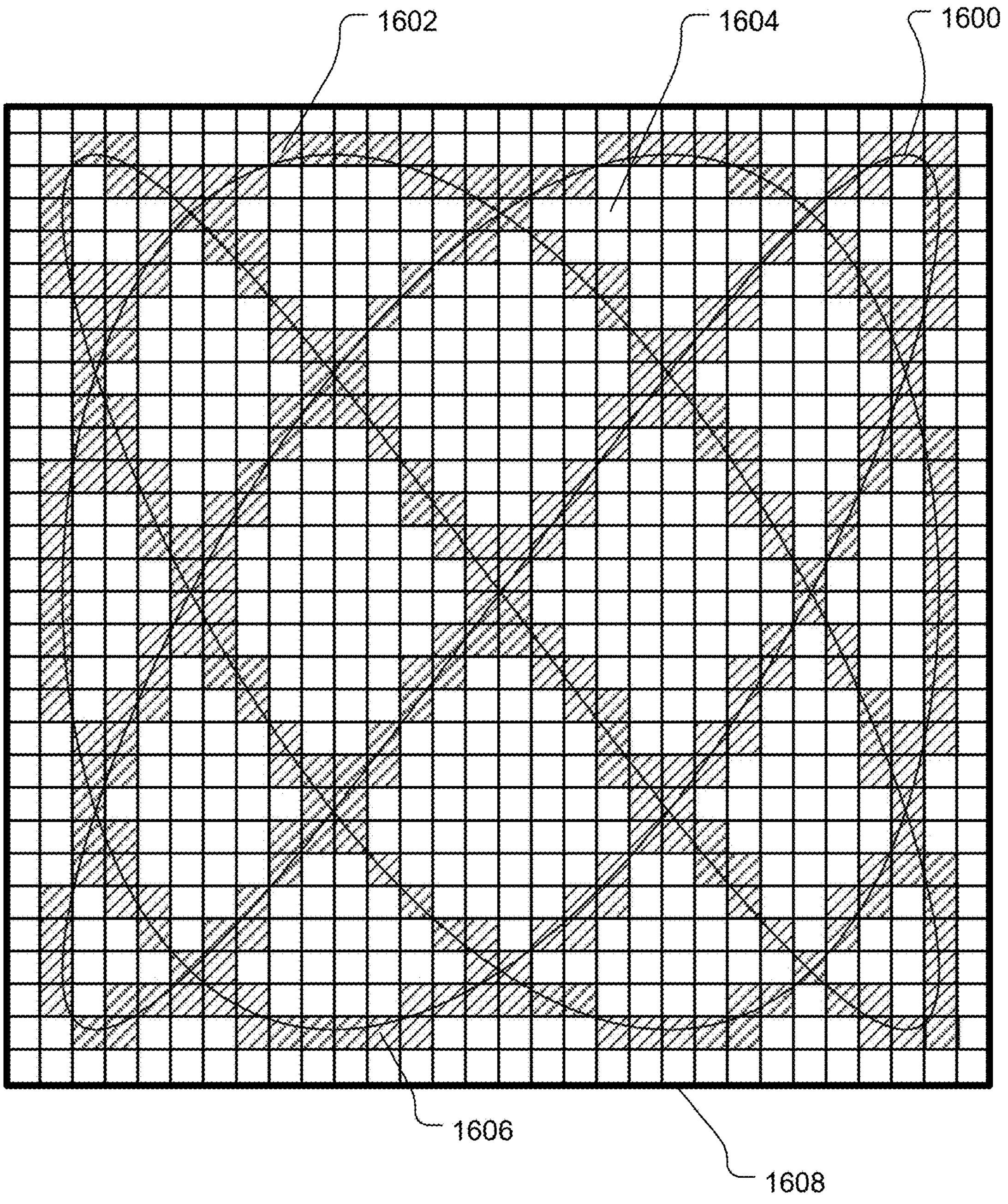
FIG. 17 indicates which pixels of FIG. 16 are illuminated by a sample arm during an exemplary hypothetical calibration process, i.e., pixels that are "identified in the calibration process," according to an embodiment of the present disclosure.

Once detected, the illuminated pixels 1602-1606 in the visible light image, and their x-y coordinates, can be stored for use in a later color mapping process. FIG. 17 indicates which pixels are illuminated with cross-hatching. For example, pixels 1602 and 1606 are illuminated. These pixels 1602, 1606 are referred to herein as being "identified in the calibration process." Thereafter, when the system later colors pixels or voxels of a dense 3D model based on OCT data, the color mapping process may use only pixels from the visible image camera 1460 whose coordinates are those that were identified in the calibration process.

Figure 18:
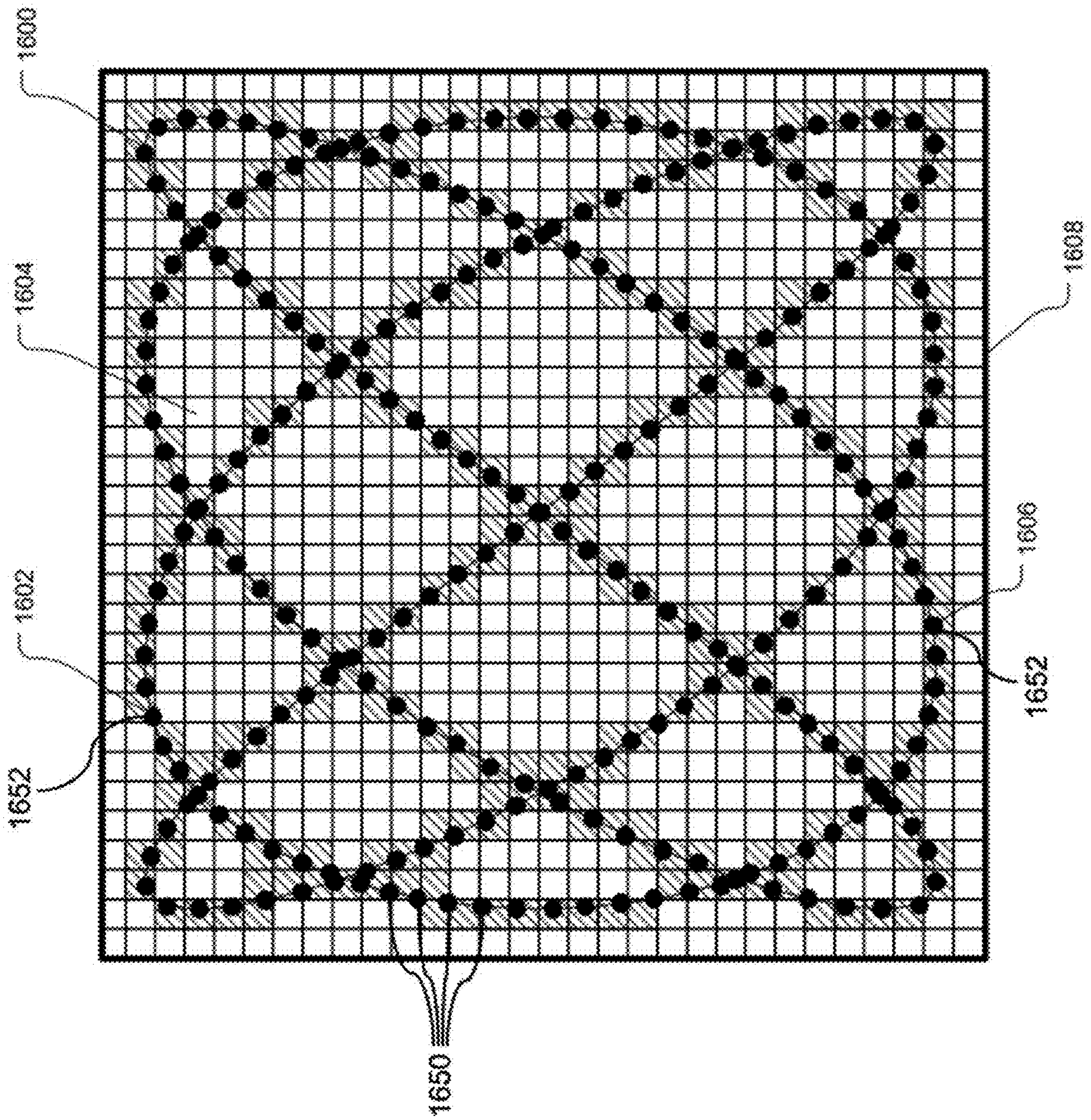
FIG. 18 indicates the locations of A-scans relative to the illuminated pixels shown in FIG. 16.

FIG. 18 illustrates schematically the locations 1650 at which individual A-scans are performed when carrying out the scanning pattern. The particular A-scans 1652 corresponding to pixels 1602 and 1606 are indicated. During the later generation of a 3D model of the object being scanned, each A-scan may be used to determine a surface point on the object. By knowing a correspondence between the image pixels of the visible light camera and the A-scans of the scanning pattern, it is possible to determine coloring or texturing parameters associated with that surface point. Hence (or otherwise), when surface points are added to the 3D model, it is possible to determine how to color or texture them.

In some arrangements, to determine the image pixels that are associated with a particular A-scan, a distance from the scanner to each surface point can be used. This is particularly (but not exclusively) applicable in systems like that of FIG. 15A, where the field of view of the camera is angled relative to the optical axis of the sample beam. This is because the 3D surface shape of the object makes the scanning pattern appear distorted from the vantage point of the camera. However, the detected distance for each A-scan can be used to correct for these distortions, e.g., by applying a geometric transform to identify the image pixels corresponding to each A-scan.

Figure 19:
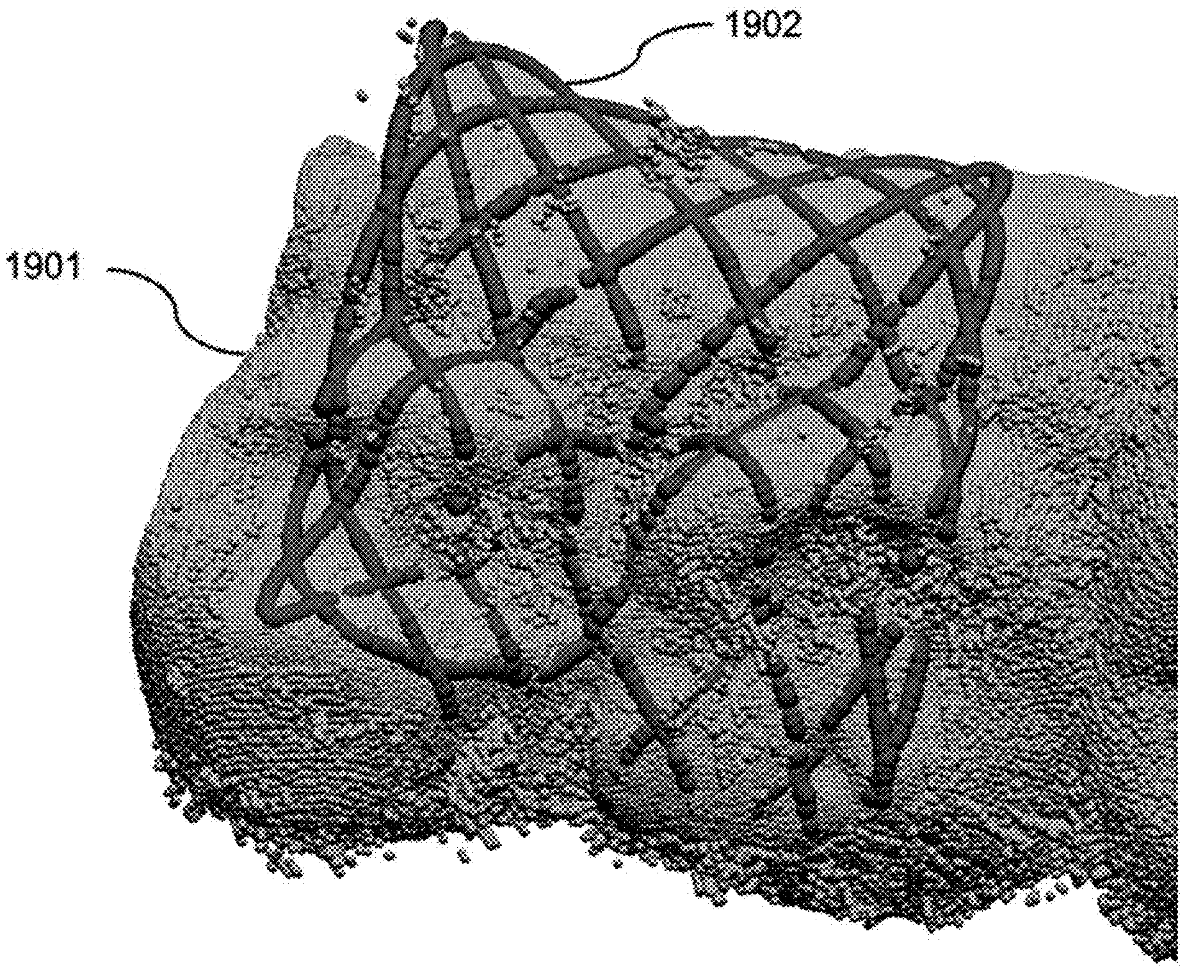
FIG. 19 illustrates a 3D model of a tooth, to which additional surface portions are being added.

FIG. 19 illustrates a 3D model being generated based on a plurality of sparse sets of volumetric OCT scanning data. The existing model 1901, at a particular point in time, is shown in light grey. As may be seen, the 3D model comprises a plurality of exterior surface portions. In the particular example shown, each exterior surface portion is a voxel;

however, in other examples, each surface portion could be a flat face that forms part of a net or mesh. As is apparent, in FIG. 19, each voxel is illustrated as a small sphere in FIG. 19.

FIG. 19 shows additional surface elements 1902 (in dark grey) being added to the 3D model that are based on a further set of volumetric OCT scanning data. At this point, coloring (or texturing) parameters for the additional points may be determined for each of the additional surface elements 1902, based on associated pixels of a visible light image taken at the same time that the further set of volumetric OCT scanning data was captured. A visualization of the colored 3D model may then be presented to the user. In this way (or otherwise), a 3D model may be progressively, or iteratively generated and colored, for example in real time. Generating a colored 3D model of the object being scanned in real time may assist a user in identifying areas of the object that are incompletely or ineffectively scanned.

Color Mapping with Angled Camera

Figure 20:
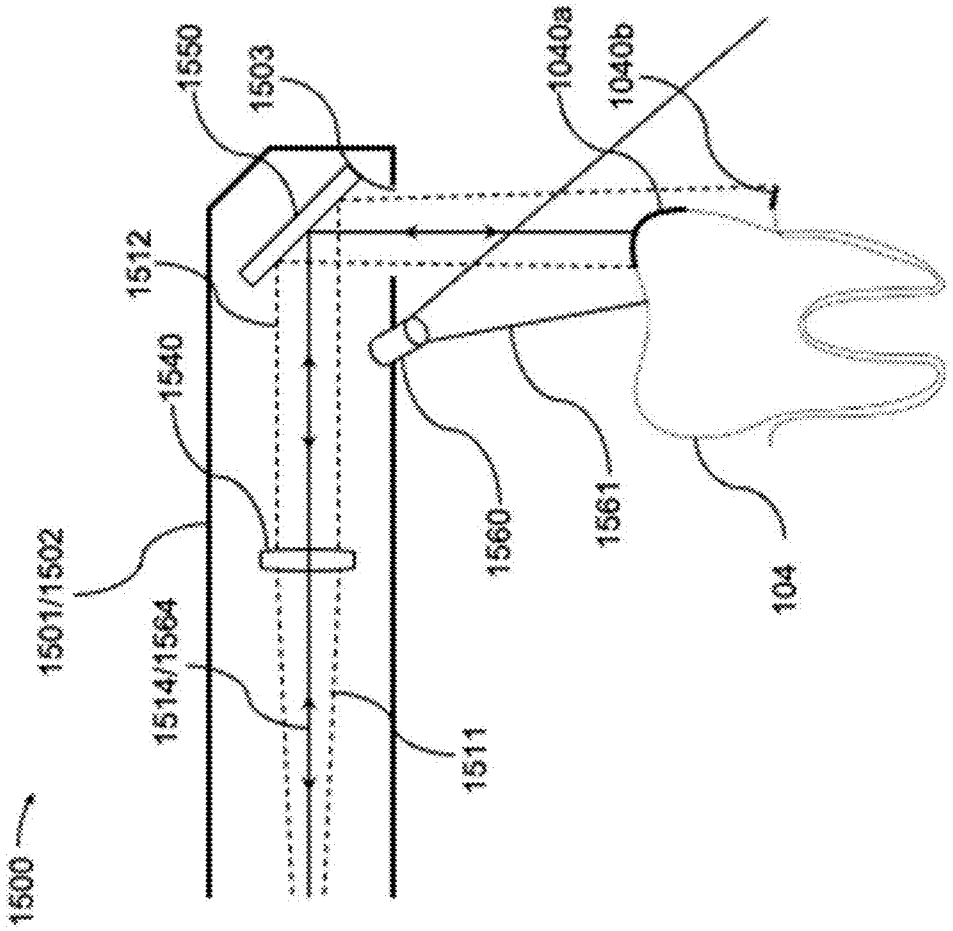
FIG. 20 is a schematic diagram showing the OCT system of FIG. 15A concurrently capturing a volumetric OCT frame and a visible light image of part of a subject's dental anatomy.
Figure 21:
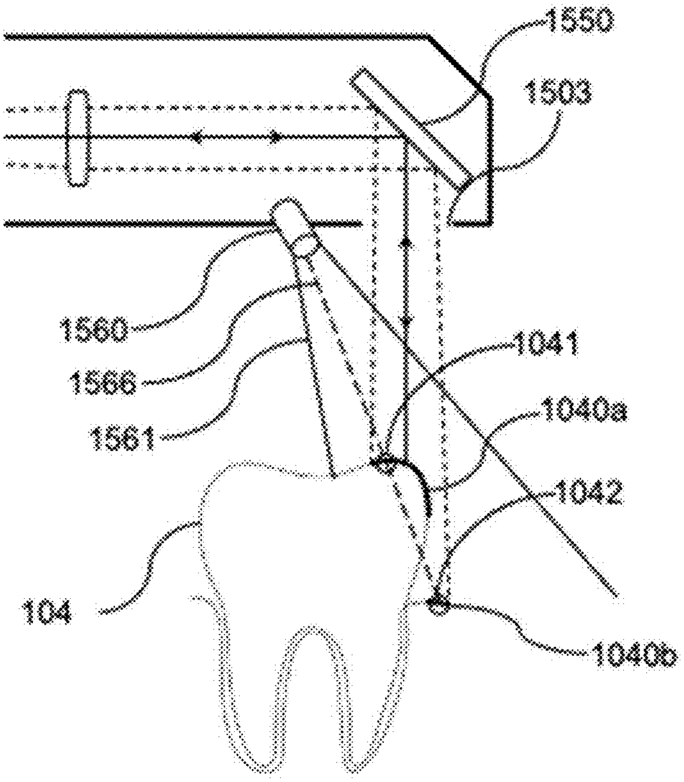
FIG. 21 illustrates an example of two surface points identified in a volumetric OCT frame that project onto the same pixel of a visible light camera.

Reference is now directed to FIG. 20, which is a schematic diagram showing the OCT system 1500 of FIG. 15A concurrently capturing a volumetric OCT frame and a visible light image (using camera 1560) of part of a subject's dental anatomy 104. As shown, when capturing the volumetric OCT frame, the sample beam 1514 addresses both a part of one of the subject's teeth 1040*a*, and a part of the gingiva 1040*b* associated with the tooth. However, because the optical axis 1561 of the camera 1560 is angled with respect to the central axis 1515 of the sample beam 1514, while the same part of the subject's tooth 1040*a* is visible to the camera 1560, at least some of the associated part of the gingiva 1040*b* is not visible to the camera 1560, because it is obscured by the subject's tooth. This is highlighted in FIG. 21, which shows, with dashed line, a ray 1566 projected from one of the pixels of the camera 1560. As is apparent, this ray 1566 extends to a point 1041 on the surface of the tooth. However, as shown, if the tooth were not present the ray 1566 would extend to a point 1042 on the surface of the associated gingiva. Consequently, if the visualization technique described above with reference to FIG. 19 were applied, the 3D model generated might include an exterior surface portion corresponding to point 1042 that is colored in accordance with an image pixel depicting point 1041 on the surface of the tooth. More broadly, what might result is that the parts of the 3D model that correspond to the gingiva, but which are obscured by the teeth, would be colored as if they were teeth. While such a visualization can still be useful to the user (and, in any case, the visualization may self-correct once the scanner is moved so that the obscured parts of the gingiva are visible to the camera), it would be preferable to avoid such unexpected coloring in the 3D model. Accordingly, reference is directed to FIGS. 22 and 23, which illustrate an approach to address such unexpected coloring of surface portions, according to an aspect of the present disclosure.

Figure 22:
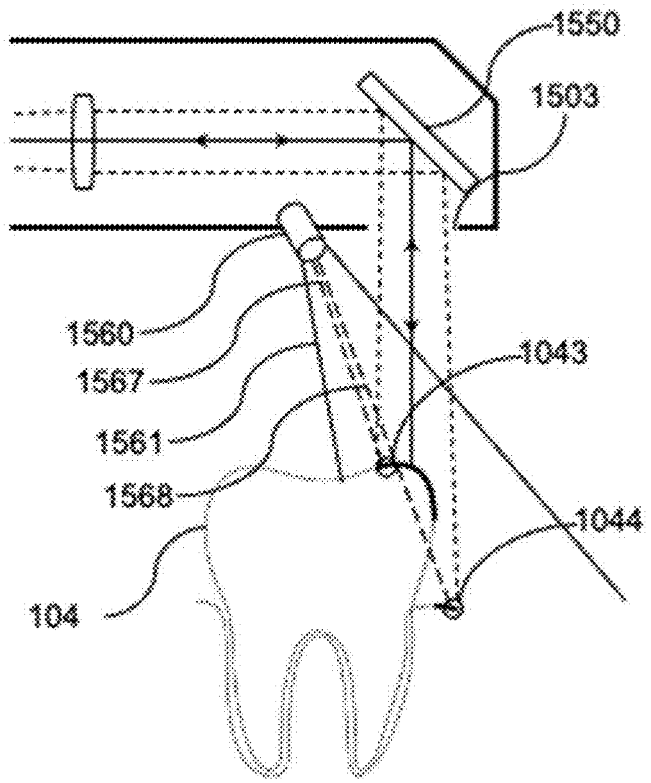
FIG. 22 illustrates an example of two surface points identified in a volumetric OCT frame that project onto nearby pixels of a visible light camera.

FIG. 22 shows two exterior surface points 1043, 1044 on the subject's dental anatomy 104 that have been identified in the OCT volumetric frame. As will be appreciated, these two points 1043, 1044 are among a large number of exterior surface points, each of which corresponds to one of the A-scans performed when capturing the volumetric OCT frame. As discussed elsewhere herein, such exterior surface points can, for example, be identified by applying an edge detection algorithm to the A-scan data captured in the OCT volumetric frame.

As exemplified by the respective lines 1567 and 1568 for the two exterior surface points 1043, 1044, an association is then determined between each of the large number of exterior surface points identified for the volumetric OCT frame and a respective subset of pixels in the image captured by the camera 1560. This association can, for example, be determined by applying a matrix that transforms the 3D locations of the points in the coordinate system for the volumetric OCT surface image to a coordinate system for the camera, where two of the coordinates correspond to u, v pixel location coordinates and a third corresponds to distance from the camera. Once a u, v pixel location coordinate has been determined for a particular surface point, a subset of pixels at that location can then be associated with the surface point.

Figure 23:
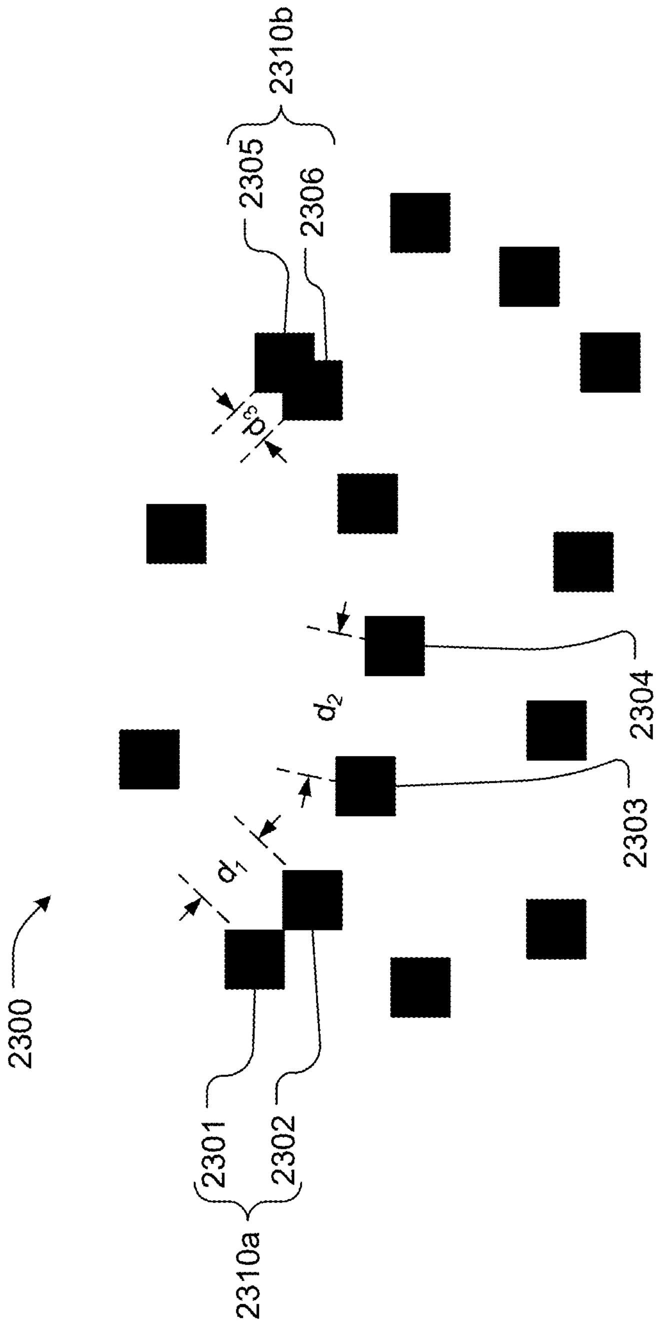
FIG. 23 illustrates subsets of image pixels that are associated with respective surface points identified in a volumetric OCT frame.

Each subset of pixels can, for example, have the same shape, as is the case in the example shown in FIG. 23, which illustrates of a number of subsets of pixels 2301, 2302, 2303, 2304, 2305, 2306 that have been identified within an image 2300. In the particular example shown in FIG. 23, each subset of pixels 2301, 2302, 2303, 2304, 2305, 2306 consists of a square block of 4 pixels. However, in other examples each subset of pixels or could be have any suitable shape, for example being circle shaped, or square shaped, and/or could have any suitable size, even consisting of only 1 pixel. Furthermore, it is not essential that each subset is the same size; for example, the size of each subset may depend on the distance of the corresponding exterior surface point from the camera, for instance so that larger subsets are associated with exterior surface points closer to the camera.

Having thus determined an association between each exterior surface point and a respective subset of pixels, the system 1500 then determines spacings between the subsets of pixels 2301, 2302, 2303, 2304, 2305, 2306. In FIG. 23, for clarity, only three exemplary spacings d1, d2, d3 are indicated, but it will be appreciated that spacings between substantially all of the subsets may, in some examples, be determined.

Using the thus-determined spacings, the system 1500 identifies groups of potentially mutually obscuring subsets of pixels. For instance, in the example shown in FIG. 23, subsets 2301 and 2302 have been identified as one group 2310*a* of potentially mutually obscuring subsets of pixels, and subsets 2305 and 2306 have been identified as another group 2310*b* of potentially mutually obscuring subsets of pixels. To identify groups of potentially mutually obscuring subsets of pixels, the system 1500 can, for example, simply determine which of the spacings d1, d2, d3 is below a fixed threshold (which could, in some examples be zero, so that only co-located subsets are identified as a mutually obscuring group). However, in a more complex example, the system 1500 may take into account the relative distances from the camera of the subsets, for instance applying a larger pixel spacing threshold for two subsets whose distances from the camera differ substantially (e.g., because the "shadow" cast by a subset increases with increasing distance from the camera, so that it can more easily obscure subsets much further away from the camera).

As will be appreciated, each thus-identified group of potentially mutually obscuring subsets of pixels corresponds to a group of exterior surface points, which can therefore be referred to as a group of potentially mutually obscuring points. When a 3D model of the anatomical item 104 is generated using the approach discussed above with reference to FIG. 19, exterior surface portions that are based on such potentially mutually obscuring points can be treated differently when determining coloring parameters.

More particularly, for an exterior surface portion that has been generated based on one of a group of potentially mutually obscuring points, color parameters for the exterior surface portion can be determined based the proximity of the point in question to the camera, relative to the proximity to the camera of each of the other potentially mutually obscuring points in the same group.

In one example, the system determines whether the point in question is closer than all other potentially mutually obscuring points in the same group, and, only if so are the coloring parameters for the exterior surface portion based on the subset of pixels corresponding to the point in question. For example, consider the case where points 1043 and 1044 shown in FIG. 22 have been identified as a group of mutually obscuring points. When determining coloring parameters for an exterior surface portion corresponding to/based on point 1044, such coloring parameters would not be based on the subset of pixels associated with point 1044, because point 1044 is not the closest to the camera of its group of mutually obscuring points—point 1043 is. The coloring parameters for point 1044 could therefore, in some examples, be determined based on a predetermined contrast color, which can, for example, be a color not typically present in the type of anatomical item under study. For instance, the contrast color could be bright green.

In other examples, the system may determine whether a difference in distances from the camera for some or all members of the group is below some threshold amount (e.g., a small distance such as 1 mm or less). In such a situation, for the corresponding exterior surface portions it may be acceptable to determine coloring parameters based on the respective pixel subsets associated with the members of the group, or to determine the coloring parameters based on the pixel subset associated with the member of the group closest to the camera.

OCT System with Distally-Located Camera

In the embodiments of an OCT system described above with reference to FIGS. 15A and 15B it was noted that the camera 1560, 1560' and the window 1503, 1503' are disposed at a distal end of the scanning device 1501, 1501', with an optical axis 1565 of the camera 1560, 1560' being oriented towards a region exterior the scanning device, adjacent the imaging window 1503, 1503'. The inventors consider that color mapping OCT systems with such an arrangement of the camera 1560, 1560' may be particularly simple to calibrate and/or may be particularly simple/inexpensive to manufacture.

Regarding calibration, because the camera directly images the exterior of the scanning device 1501, 1501', rather than relying on optical elements such as mirrors, beam splitters and lenses to receive light, the image received by the camera is typically more intensive and/or less distorted. Consequently, the spots generated on a calibration object can be more easily identified and analyzed in the images generated by the camera.

Regarding manufacturing, it should be noted that a camera used for color mapping should have a relatively wide field of view so as to image as many as possible of the exterior surface points on the anatomical item that have been identified from the volumetric OCT frame. However, the location and pattern of such points, as viewed from the camera, will vary significantly depending on the surface geometry of the anatomical item. On the other hand, if a camera is arranged at a significant optical distance from the anatomical item, like the camera 1460 in the example of FIG. 14, manufacturing a lens that provides such a wide field of view is typically costly and/or complex.

The inventors further consider that, because such benefits are derived from the optical components, and are not specific to a particular color mapping OCT scheme, color mapping OCT systems with the camera and the window disposed at a distal end of the scanning device, with an optical axis of the camera being oriented towards a region exterior the scanning device can be utilised with color mapping OCT schemes other than those described above.

Optical Coherence Tomography (OCT)

Optical coherence tomography (OCT) is an imaging technique that uses low-coherence, typically near-infrared, light to capture micrometer-resolution, two- and three-dimensional images from within optical scattering media, such as biological tissue. OCT is based on low-coherence interferometry. In conventional interferometry with long coherence length, i.e., laser interferometry, interference of light occurs over a distance of meters. However, in OCT, this interference is shortened to a distance of micrometers, due to the use of broad-bandwidth light sources, i.e., sources that emit light over broad ranges of wavelengths, such as superluminescent diodes and lasers with extremely short pulses (femtosecond lasers).

FIG. 1 is a schematic block diagram of an optical coherence tomography system 100, according to the prior art. Light in the OCT system 100 is broken into two arms: a sample arm 102 containing an item under test 104, and a reference arm 106, usually containing a mirror 108. A combination of reflected light from the sample arm 102 and reference light from the reference arm 106 gives rise to an interference pattern, but only if the light from both arms 102 and 106 have traveled equal optical distances, i.e., distances that differ by less than a coherence length of the light. By scanning the mirror 108 in the reference arm 106, a reflectivity profile of various depths of the item 104 can be obtained. The amount of interference is proportional to the amount of reflected light, which enables distinguishing portions of the item under test 104 having different reflectivity characteristics at different depths. Any light that is outside the short coherence length does not interfere, enabling the OCT to interrogate specific depths of the item under test 104 and produce the reflectivity profile. The reflectivity profile, called an A-scan, contains information about spatial dimensions and structures within the item of interest. An A-scan (axial or depth scan) represents data recovered from various depths of single "hole" conceptually "drilled" into the item under test 104.

Figure 2:
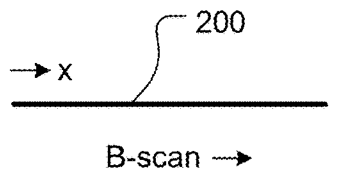
(Prior Art) Fig. 2
FIG. 2 illustrates a line segment on a surface of an item under test, according to the prior art.

A cross-sectional tomogram (B-scan) may be achieved by laterally combining a series of these axial depth scans (A-scans) or scanning a mirror 110 in the sample arm 102. For example, scanning the mirror 110 in one dimension moves the light of the sample arm 102, so as to project the light onto progressive points along a line segment (as viewed down the sample arm 102 axis 112) on a surface of the item under test 104. Line 200 in FIG. 2 illustrates the line segment on the surface of the item under test 104. Modern OCT systems sample individual points along the line 200, yielding individual pixels (not shown) along the line 200.

Figure 3:
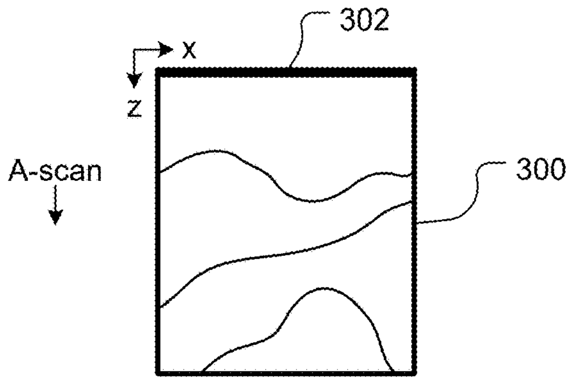
(Prior Art) Fig. 3
FIG. 3 illustrates an exemplary combination of multiple A-scans along a B-scan to produce a two-dimensional reflectivity profile, according to the prior art.

An OCT system can combine multiple A-scans along a B-scan to produce a two-dimensional reflectivity profile, for example as illustrated at 300 in FIG. 3. The plane of two-dimensional reflectivity profile 300 represents a "slice" taken through the item under test 104. The top line 302

(shown in heavy line) of the two-dimensional reflectivity profile 300 of FIG. 3 corresponds to the line 200 in FIG. 2.

Figure 4:
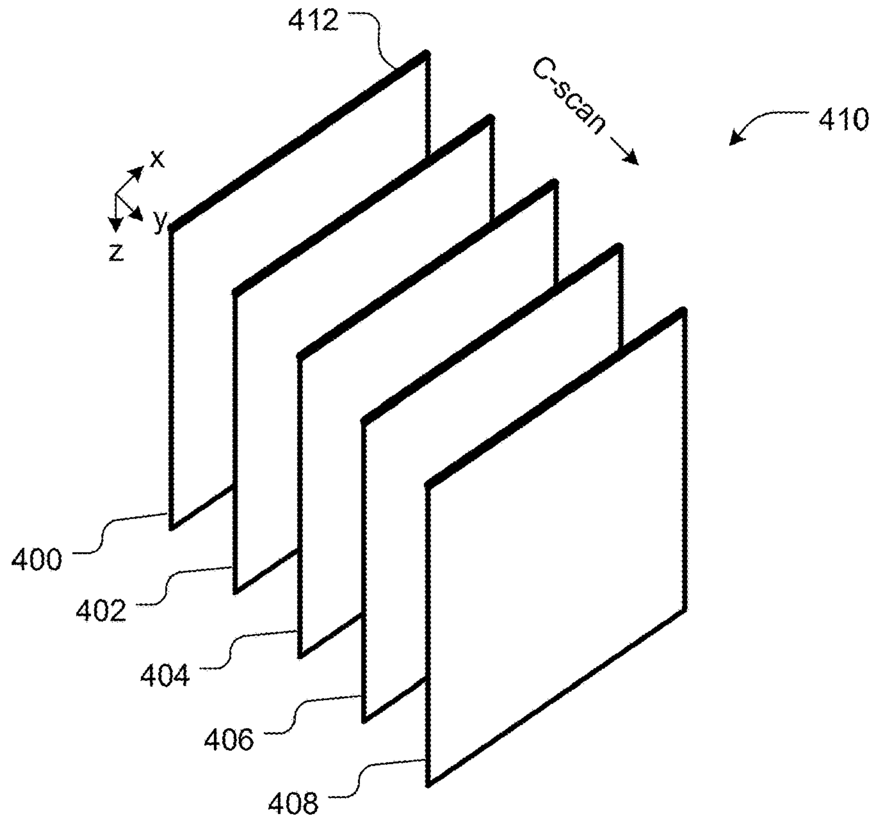
(Prior Art) Fig. 4
FIG. 4 illustrates an exemplary combination of multiple A/B scans along a C-scan to produce a three-dimensional reflectivity profile using a raster scan, according to the prior art.

An OCT system can combine multiple A/B scans, for example as represented by scans 400, 402, 404, 406, and 408 in FIG. 4, to produce a three-dimensional reflectivity profile 410. Top heavy lines in FIG. 4, represented by heavy line 412, correspond to line 300 in FIG. 3 and line 200 in FIG. 2.

Figure 5:
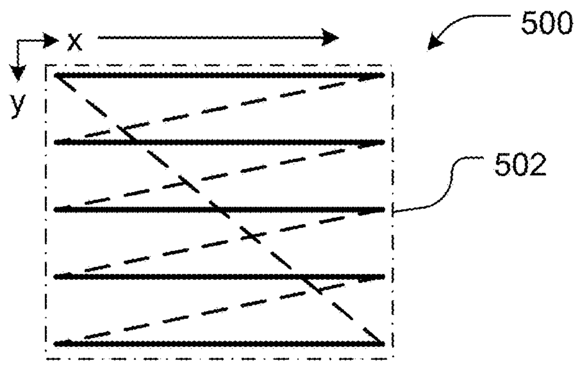
(Prior Art) Fig. 5
FIG. 5 illustrates a conventional raster, according to the prior art.

A conventional approach to performing a combined B/C scan is to cause the reference arm light beam to be projected toward the item under test 104 onto progressive points along a raster 500, as illustrated in FIG. 5. A raster is characterized by a plurality of parallel, spaced-apart scan line segments. FIG. 5 illustrates retrace line segments in dashed line and a direction of scan by an arrow. However, depending on how the light of the reference arm is redirected, the raster may have no retrace line segments. For example, two rotating polygon mirrors can produce a raster without a retrace.

One complete raster scan, i.e., one traversal of a pattern, like the one shown in FIG. 5, is referred to as a frame. A region generally covered by one traversal of the pattern is referred to as being outlined by a two-dimensional scan area outer boundary or bounding box, as exemplified by two-dimensional scan area outer boundary 502.

Figure 6:
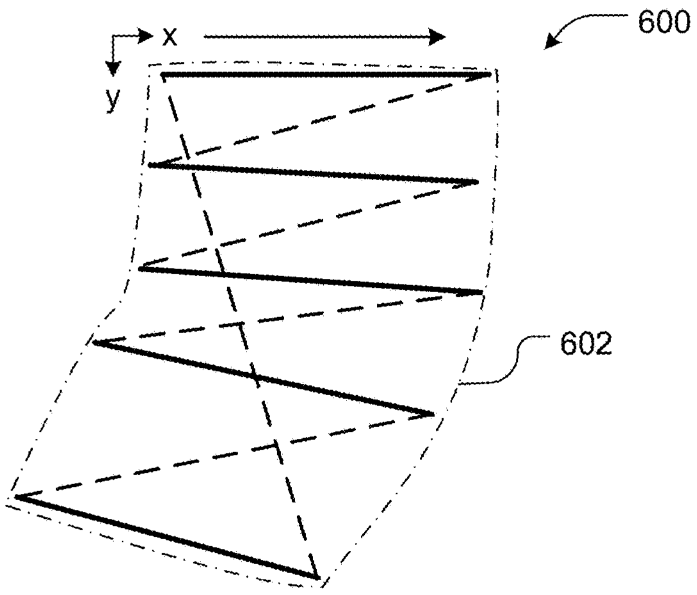
(Prior Art) Fig. 6
FIG. 6 illustrates a problem (motion blur) conventional raster scans exhibit, due to movement of a scanning wand during a frame, according to the prior art.

Unfortunately, conventional intraoral OCT scanning methods and apparatus are too slow, particularly for hand-held scanning wands. A conventional single-frame raster scan would take on the order of several seconds to complete, during which time the system would experience an unacceptable amount of motion blur due to movement of a patient or unintended movement of a hand of a human operator. For example, as illustrated in FIG. 6, unintended movement of a scanning wand could result in: uneven spacing between successive raster line segments, x and/or y distortion of the raster pattern leading to x and/or y distortion of the two-dimensional scan area outer boundary 602, and curvature (not shown) of individual raster line segments. Furthermore, it is impossible to estimate an extent of the motion blur, because a single raster pattern has no sample point where two raster lines cross. Therefore, no common reference points exist, where two raster line segments interrogate the same point on an item under test and can, therefore, be used to detect or measure the unintended movement. Some prior art systems include an additional camera to detect the unintended movement, but such systems are big, expensive, and awkward to use.

A conventional OCT scan frame typically covers too small an area to completely image a large tooth or a relatively large portion of a mouth. Consequently, multiple OCT scan frames must be combined to form a single image of item(s) under test. However, holding a scanning wand still for each such frame, and controllably moving the wand only between frames, is extremely challenging or impossible for a human operator.

Figure 7:
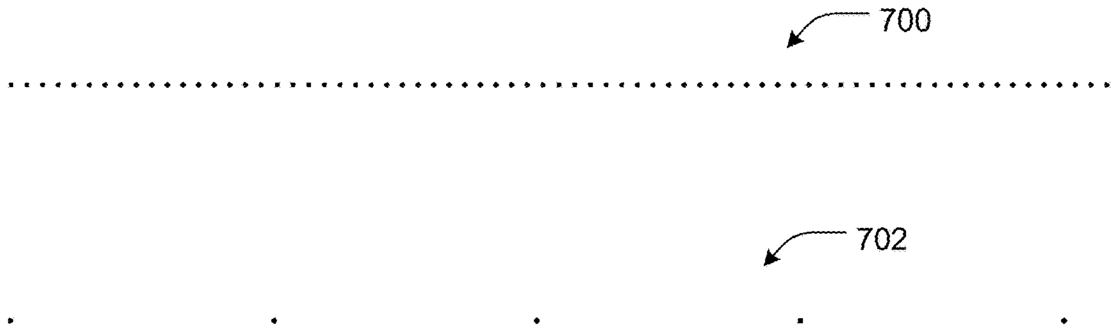
FIG. 7 illustrates a hypothetical conventional OCT system dense scan line segment consisting of individual sample points (pixels), as well as a hypothetical sparse scan line segment of an embodiment of the present invention.

Embodiments of the present disclosure solve these and other problems associated with prior art OCT scanning technology. To avoid unacceptable amounts of motion blur, these embodiments traverse their respective scan patterns quickly, typically completing an entire two-dimensional frame faster than a conventional raster scanner completes one raster line segment. In order to traverse their scan patterns quickly, these embodiments take fewer A-scans per length of scan pattern than conventional OCT scanners. In other words, if conventional scanners are characterized as conducting "dense" scans, these embodiments conduct "sparse" scans. Recall from the discussion of FIG. 2 that OCT systems sample individual points along the line 200, yielding individual pixels (not shown) along the line 200. FIG. 7 illustrates a hypothetical conventional OCT system dense scan line segment 700 consisting of individual sample points (pixels), as well as a hypothetical sparse scan line segment 702 of an embodiment of the present invention. Notice that the sample points of the line segment 700 are much more densely positioned along the line than the sample points along the line segment 702, although the specific ratio of sample spacings shown in FIG. 7 is merely for illustration.

Figure 8:
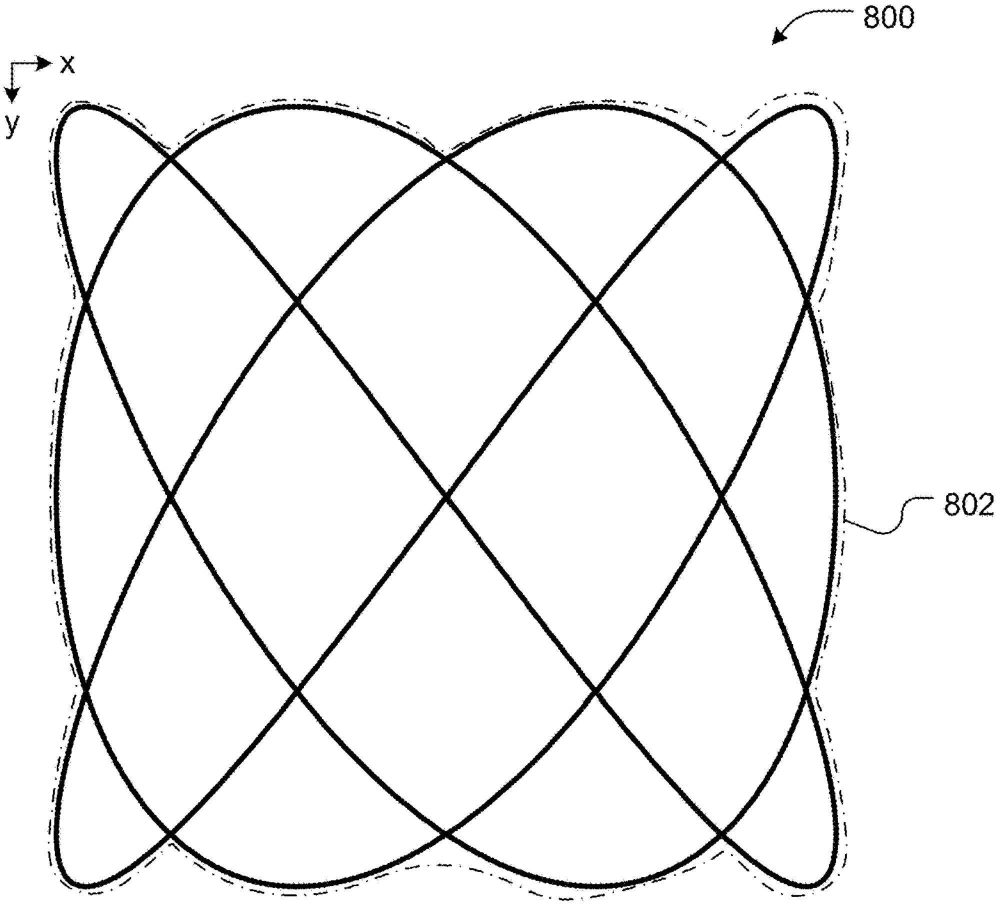
FIG. 8 illustrates an exemplary Lissajous figure used by embodiments of the present invention.

Embodiments of the present invention utilize curved scan patterns, such as Lissajous figures or spirals, so each traversal of the scan pattern can yield information sufficient to extract a surface of the scanned item. In other words, the scan pattern must cover a 2D field of view. FIG. 8 illustrates an exemplary Lissajous FIG. 800.

Figure 9:
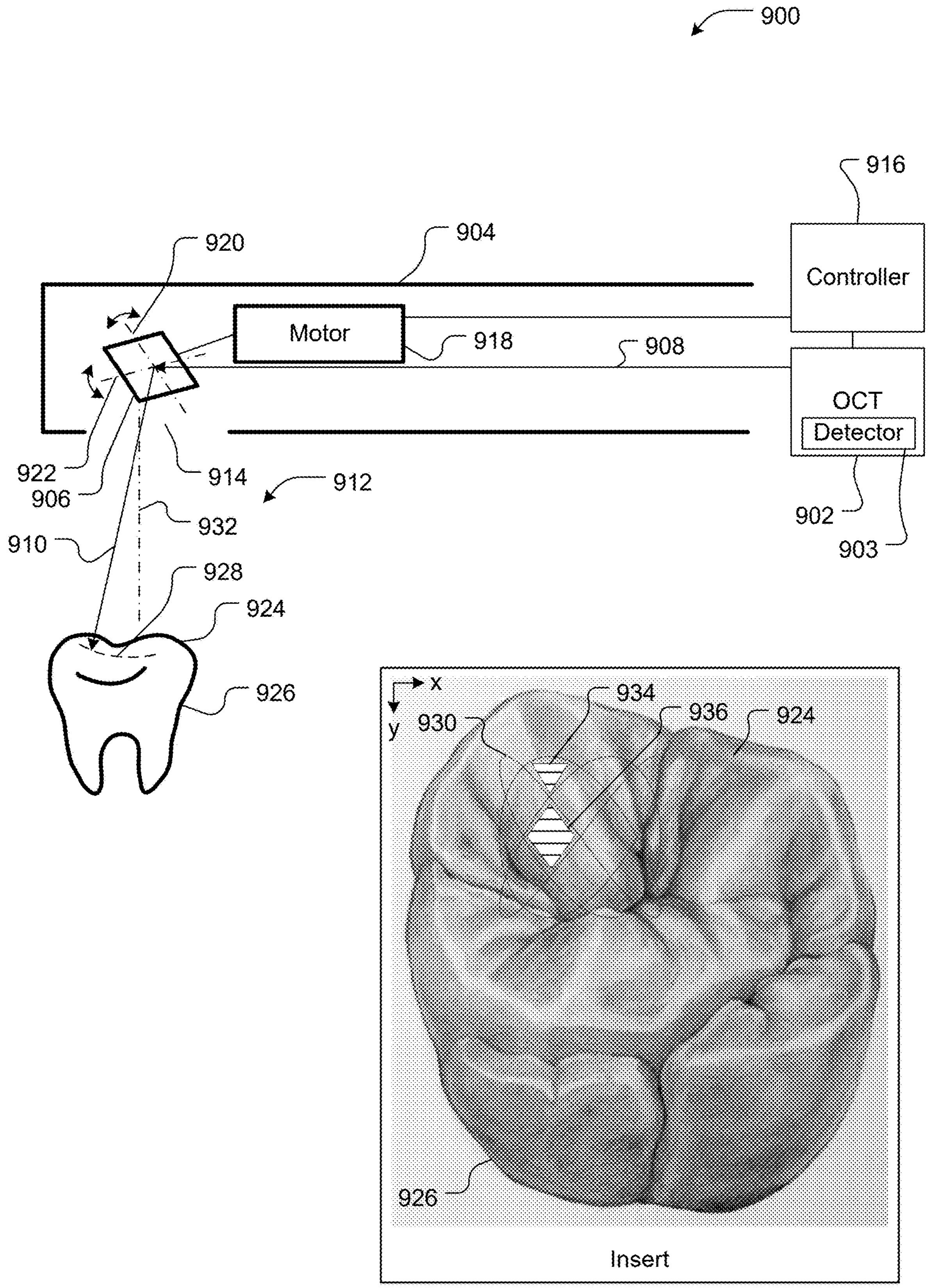
FIG. 9 is a schematic block diagram of a tomography system, according to embodiments of the present invention. An Insert in FIG. 9 illustrates an aspect of using the tomography system of FIG. 9.
Figure 10:
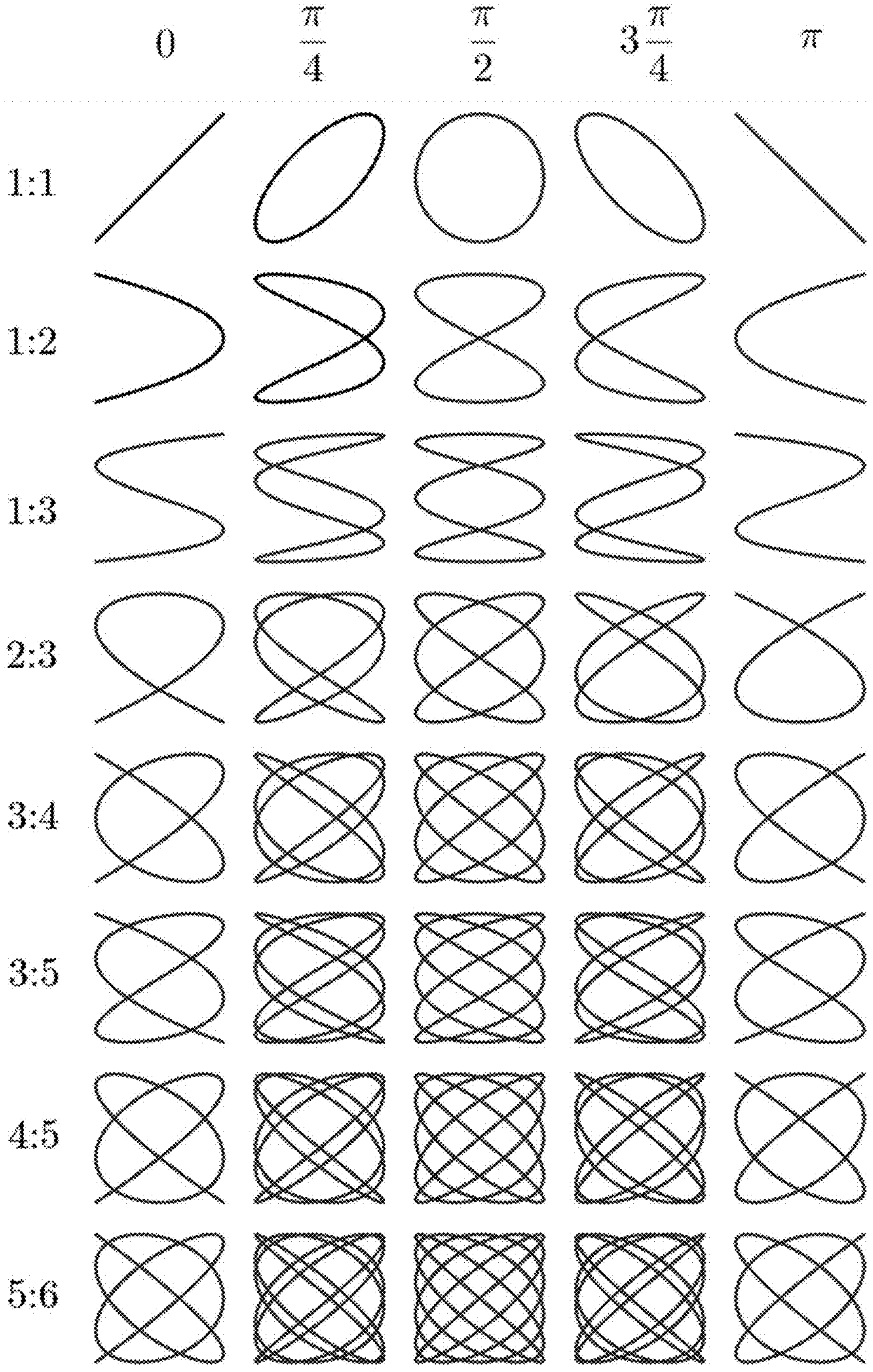
FIG. 10 illustrates other exemplary Lissajous figures that may be used by embodiments of the present invention.

As shown schematically in FIG. 9, a tomography system 900 according to an embodiment of the present invention includes an OCT system 902 with an optical detector 903, a probe housing 904 of a scanning wand, and a movable mirror system 906 disposed within the housing. The mirror system 906 is configured to redirect, such as by reflecting, a portion of a sample arm 908 of the OCT system 902. A redirected portion 910 of the sample arm 908 extends outside the probe housing 904, into free space 912, via a window 914 in the probe housing 904. A controller 916 drives a motor 918 to repeatedly alter orientation of the mirror system 906 about two different axes (exemplified by axes at 920 and 922) to thereby repeatedly scan a surface 924 of an anatomic item under test 926 with light of the sample arm 908 along a trajectory 928 according to a deterministic smooth two-dimensional scan pattern, exemplified by Lissajous pattern 930 shown in an Insert of the drawing. If the motor 918 oscillates the mirror system 906 about the two orthogonal axes 920 and 922 according to respective sine wave signals, a suitable Lissajous pattern can be achieved, based on relative frequencies and phases of the sine wave signals. Other exemplary Lissajous figures are shown in FIG. 10. As noted, other scan patterns may be used.

Returning momentarily to FIG. 8, a dashed line 802 indicates an elastic bounding shape around the Lissajous FIG. 800. As used herein, the term two-dimensional scan area outer boundary means a single closed loop elastic bounding shape tightly fitted to enclose an entire scan pattern, as exemplified by the dashed line 802, and as viewed down an axis 932 (FIG. 9) of the sample arm 908, toward the item 926, i.e., as projected onto the surface 924 of the item 926. A locus of points on the anatomic item 926 that is illuminated by the sample arm 908 during a scan may have a shape distorted from the scan pattern, as viewed from a perspective other than from the window 914, due to topography of the surface 924.

Figure 11:
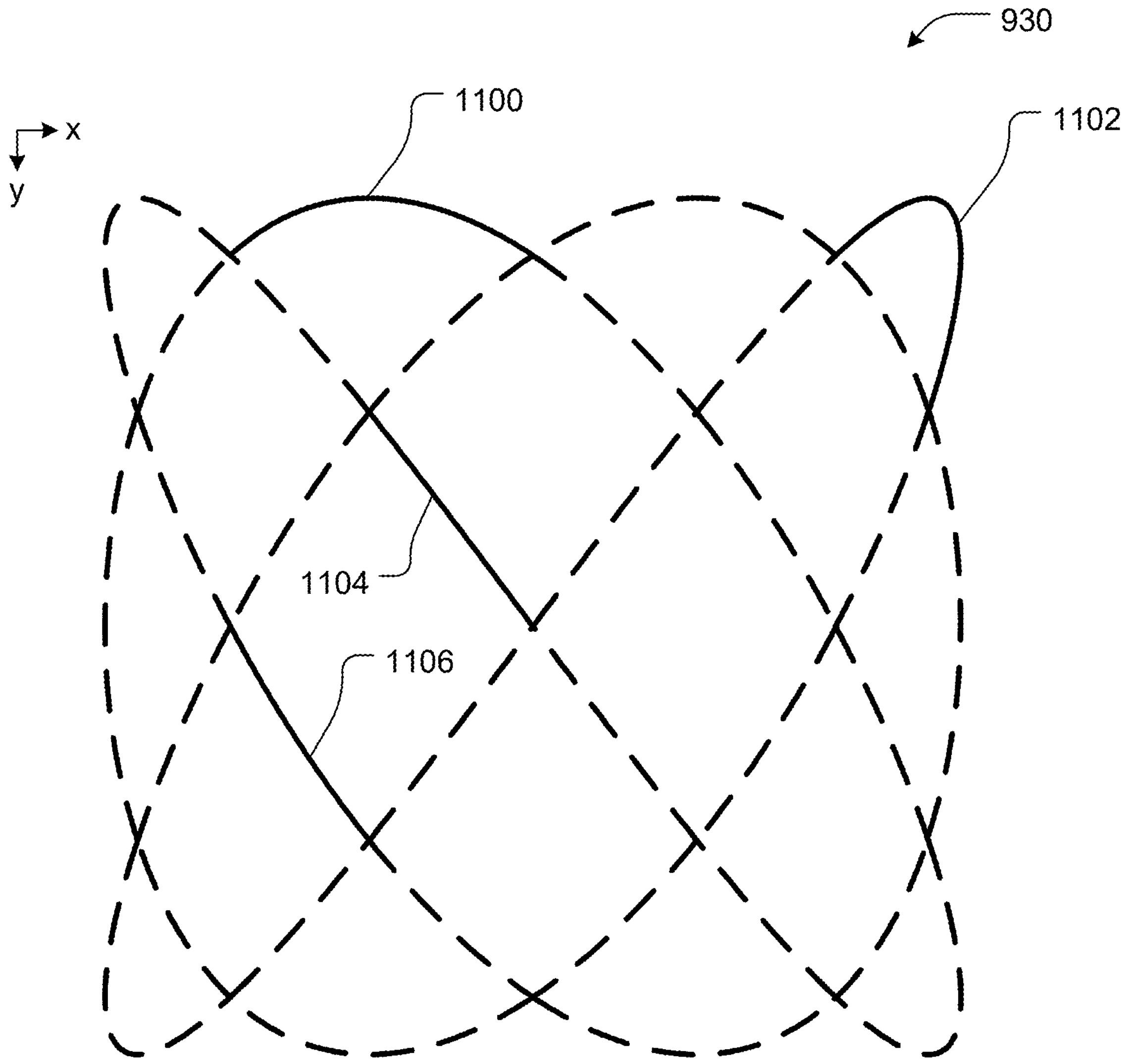
FIG. 11 shows the Lissajous figure of FIG. 9, largely in dashed line, to illustrate a concept of line segments, in relation to embodiments of the present invention.

Although, in each frame, the tomography system 900 of FIG. 9 scans portions of the item under test 926 within the two-dimensional scan area outer boundary, each frame includes samples from only a subset of the area of the two-dimensional scan area outer boundary. Specifically, each frame includes samples taken along a line (typically a curved and possibly self-crossing line, such as the Lissajous FIG. 930) that corresponds to the trajectory 928 of the sample arm light beam. Consequently, portions of the item 926 remain unsampled during each frame. For example, regions 934 and 936 (see FIG. 9 Insert) are unsampled by the Lissajous FIG. 930. The trajectory 928, particularly a complex trajectory, such as a Lissajous FIG. 930, can be considered to consist of a plurality of not-necessarily-straight line segments, as exemplified in FIG. 11. FIG. 11 shows the Lissajous FIG. 930, largely in dashed line. However, example line segments 1100, 1102, 1104, and 1106 are shown in solid line, for clarity. These line segments can be any length. The line segments need not necessarily begin and end at intersections with other lines or line segments of the trajectory.

Each traversal of the scan pattern defines a plurality of gaps between respective line segments of the trajectory. As noted, these gaps, exemplified by regions 934 and 936, are unilluminated by the light of the sample arm 908 during the traversal.

Figure 12:
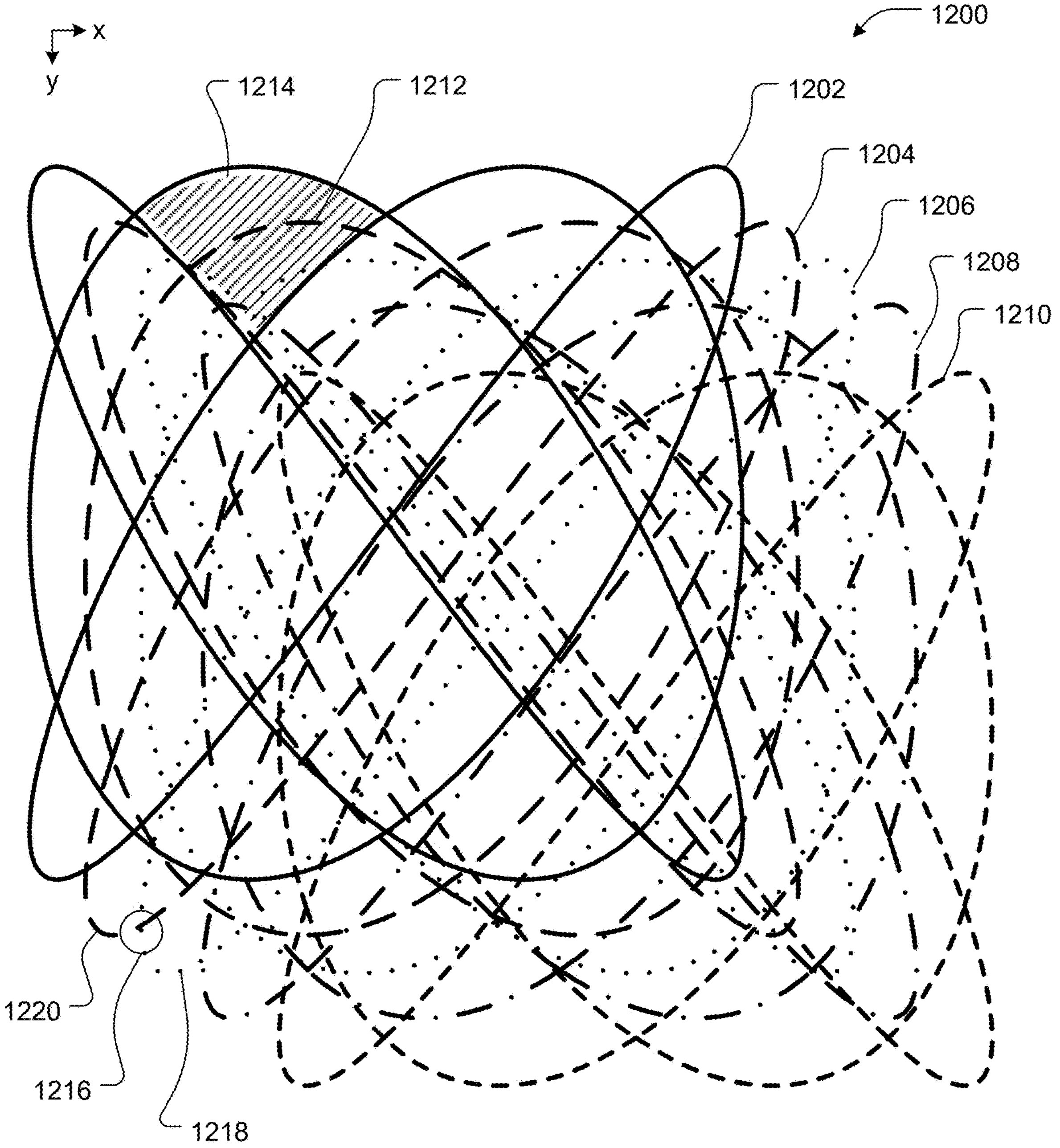
FIG. 12 illustrates a plurality of partially overlapping scan patterns, according to embodiments of the present invention.

To compensate for the sparsity of the sample points along their respective scan line segments discussed with respect to FIG. 7, and for the gaps between respective line segments of the trajectory discussed with respect to FIG. 9, embodiments of the present invention acquire and combine several partially overlapping frames for each study, as schematically illustrated in FIG. 12. For simplicity of explanation, the Lissajous figures of FIGS. 8, 9, and 11 are used as the scan pattern. However, other scan patterns can be used, as discussed in more detail herein. Each such frame is acquired from a different point of view, relative to the item under test, as exemplified in FIG. 13. These viewpoints result from a human operator or machine translating a scanning wand 1300 in space along a path 1302 proximate the anatomical item under test 1304, such as a tooth in a live patient. Thus, embodiments of the present invention take advantage of movement of the scanning wand 1300, rather than attempt to suppress the movement, as in the prior art.

FIG. 12 illustrates an exemplary plurality 1200 of successive traversals of the scan pattern 930 (FIG. 9), including a first traversal 1202, a second traversal 1204, a third traversal 1206, a fourth traversal 1208, and a fifth traversal 1210. For clarity of the drawing, each traversal 1202-1210 is shown in a different line dash type. Although five traversals 1202-1210 are shown, a study can consist of any number of traversals. As noted, respective scans are performed from different locations along the path 1303 (FIG. 13) of the scanning wand 1300. In the example shown in FIG. 12, each successive scan has an upper-left corner at a progressively larger x and y coordinate than its preceding scan. Each scan has a respective scan area outer boundary (not shown in FIG. 12), and a corresponding scan area, that partially overlaps a scan area outer boundary of at least one other such scan. Successive traversals of the scan pattern illuminate respective portions of at least some of the gaps defined by at least one other such traversal of the scan pattern. For example, the second traversal 1204, such as a portion of the second traversal indicated at 1212, illuminates a portion of a gap, indicated by hash marks 1214, defined by the first traversal 1202.

For each traversal, the controller 916 (FIG. 9) receives pixel image data from the optical detector 903, about the respective portion of the surface 924 of the anatomic item 926. The pixel image data of each traversal 1202-1210 (FIG. 12) has a first pixel or voxel density. However, successive traversals 1202-1210 "fill in" portions of some of the gaps in other of the traversals 1202-1210. Thus, for a plurality of successive traversals, the controller 916 accumulates the pixel image data of the plurality of successive traversals 1202-1210 to thereby generate a surface, and optionally 3D subsurface, image having a pixel or voxel density greater than the first pixel or voxel density. Any conventional two-dimensional or three-dimensional point cloud registration methodology may be used to fill in missing pixels or voxels in a sparse image with pixels or voxels from another sparse image. For example, a boundary between air and a surface of the anatomical item 926 may be automatically extracted for each A-scan, which yields a 3D surface for each traversal of the scan pattern, i.e., each sparse OCT frame. A plurality of sparse OCT frames can then be registered together, matching surface features of partially overlapping sparse OCT frames, using conventional techniques.

Although the controller 916 generates a surface or subsurface image having a greater pixel density than each of the individual traversals 1202-1210, the controller does not rely on interpolation to achieve this increase in pixel density. In contrast, compressive sensing schemes, such as those described in U.S. Pat. No. 11,497,402, use random or pseudo-random samples to reconstruct a surface. Using compressive sensing-type data acquisition, it is possible to reconstruct a broad class of sparse signals, containing a small number of dominant components in some domain, by employing a sub-Nyquist sampling rate. Instead of applying uniformly-spaced signal measurements, as in Nyquist-based sampling, compressive sensing theory demonstrates that several types of uniformly-random sampling protocols yield successful reconstructions with high probability.

U.S. Pat. No. 11,497,402 discloses randomized sampling OCT in two spatial dimensions, x and y. X scan positions are generated from a first pseudo-random sequence, and y scan positions are determined using a second pseudo-random sequence. A two-dimensional sampling grid is determined by interleaving the x and y sequences. Sampling tuples (xi,yi) are created from xi components of the x random sampling sequence x={x1, x2, . . . , xW} and yi components of the y random sampling sequence y={x1, y2, . . . , yD}. This forms a randomized or pseudo-randomized spacing arrangement that helps reduce the number of samples required to be obtained for generating an OCT reconstruction.

On the other hand, embodiments of the present invention do not rely on randomized or pseudo-randomized spacing arrangement. As used herein, the term deterministic means not random and not pseudo-random. As noted, the controller 916 drives the motor 918 to repeatedly alter orientation of the mirror system 906 about two different axes to thereby repeatedly scan the surface 924 of the anatomic item under test 926 with light of the sample arm 908 along a trajectory 928 according to a deterministic scan pattern.

Some embodiments use the generated surface image as a map to join together voxel subsurface data from the optical detector 903. As used herein, pixel means a picture element of a one- or two-dimensional image or a voxel (a volume element of a three-dimensional image). For each traversal, the controller 916 receives voxel subsurface data from the optical detector 903 about a respective subsurface portion of the anatomic item 926. The voxel subsurface data of each traversal has a second voxel density. As in the surface accumulation case, successive traversals 1202-1210 "fill in" portions of some of the gaps in other of the traversals 1202-1210. Thus, for the plurality of successive traversals, the controller 916 accumulates the voxel subsurface data of the plurality of successive traversals to thereby generate a subsurface three-dimensional volume image having a voxel density greater than the second voxel density.

In some embodiments, the sample arm of the OCT 902 has a wavelength of about 1310 nm, the A-scan rate is about 200 kHz, the OCT lateral beam spot size is about 35 m, and the imaging range is about 16 mm. The field of view is about 8 mm by 8 mm.

Applicability to Raster Scans

Although smooth scan patterns are described herein, some embodiments employ raster scans and partially overlap two-dimensional scan area outer boundaries, as described with respect to FIG. 12. Raster lines of successive frames interleave to illuminate at least portions of gaps defined by previous raster frames.

Slight Discontinuity in Scan Pattern

Although smooth scan patters are described herein, in some embodiments, the controller is configured to drive the motor to repeatedly alter orientation of the mirror system about two different axes to thereby repeatedly scan the surface of the anatomic item with light of the sample arm along a trajectory according to a scan pattern that is smooth along at least 80% of the trajectory. For example, the scan pattern can be a spiral, with a retrace from/to the center to/from the outer edge. As used herein, the term "smooth" has its geometric meaning.

Such a system can be implemented with two galvo mirrors, or one mirror that can be reoriented in two dimensions, such as a MEMS mirror.

Motion Detection Using Intersecting Traversals of Line Segments

A place where one line segment of a scan pattern crosses (intersects) with another line segment of the same traversal of the scan pattern can provide information to quantify motion of the housing 904 (FIG. 9) between two times. For example, an intersection identified at 1216 (FIG. 12) of two line segments 1218 and 1220 of traversal 1204 can be used to quantify motion of the housing 904 between (a) a time the sample arm 908 light beam traversed line segment 1218 in the vicinity of the intersection 1216 and (b) a time the sample arm 908 light beam traversed the other line segment 1220 in the vicinity of the intersection 1216.

Ideally, if the housing 904 has not moved between times (a) and (b), the sample arm 908 light beam should interrogate the same or very similar regions of the item under test 926 in the vicinity of the intersection 1216. If, however, the controller 916 detects a significant difference, ex. greater than a predetermined amount, between portions of the item under test 926 that are interrogated by the light beam at times (a) and (b), the controller 916 may conclude that the point of view of the housing 904 has changed significantly between times (a) and (b). Optionally, the controller 916 may discard the current frame, on an assumption that the frame suffers from excessive motion blur.

Alternatively, the controller 916 may estimate an amount of change in the field of view by analyzing differences in the portions of the item under test 926 that were interrogated by the light beam at times (a) and (b). For example, based on information about a characteristic, such as reflectivity, density, or color, of the portions of the item under test 926 interrogated at times (a) and (b) and an expected spatial gradient in that characteristic of the item under test 926, the controller 916 may estimate a spatial distance between where the two samples were interrogated and, therefore, estimate an amount or rate of translation of the housing 904. The expected spatial gradient in the characteristic may be a pre-programmed assumption, or it may be a user-entered value, or the controller 916 may automatically estimate the gradient based on other samples of the item under test 926.

Definitions

As used herein, the following term shall have the following meanings, unless context indicates otherwise.

"Continually" means continuously or repeatedly, although not necessarily in perpetuity. The term continually encompasses periodically and occasionally. Continually generating a signal means generating a continuously varying signal over time or generating a series of (more than one) discrete signals over time. Continually generating a value, such as an error value, means generating a continuously varying value, such as an analog value represented by a continuously varying voltage, or generating a series of (more than one) discrete values over time, such as a series of digital or analog values.

While the invention is described through the above-described exemplary embodiments, modifications to, and variations of, the illustrated embodiments may be made without departing from the inventive concepts disclosed herein. For example, although specific parameter values, such as materials and dimensions, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

As used herein, including in the claims, an element described as being configured to perform an operation "or" another operation is met by an element that is configured to perform only one of the two operations. That is, the element need not be configured to operate in one mode in which the element performs one of the operations, and in another mode in which the element performs the other operation. The element may, however, but need not, be configured to perform more than one of the operations.

Although aspects of embodiments may be described with reference to flowcharts and/or block diagrams, functions, operations, decisions, etc. of all or a portion of each block, or a combination of blocks, may be combined, separated into separate operations or performed in other orders. References to a "module," "operation," "step" and similar terms are for convenience and not intended to limit their implementation. All or a portion of each block, module, operation, step or combination thereof may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The controller 916, etc. or portions thereof may be implemented by one or more suitable processors executing, or controlled by, instructions stored in a memory. Each processor may be a general-purpose processor, such as a central processing unit (CPU), a graphic processing unit (GPU), digital signal processor (DSP), a special purpose processor, etc., as appropriate, or combination thereof.

The memory may be random access memory (RAM), read-only memory (ROM), non-volatile memory (NVM), non-volatile random-access memory (NVRAM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, database schemas and the like, systems may be embodied using a variety of data structures, schemas, etc.

Disclosed aspects, or portions thereof, may be combined in ways not listed herein and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as “first,” “second” and “third,” are used to distinguish respective elements, such as mirrors or traversals, from one another and are not intended to indicate any particular order or total number of mirrors or traversals in any particular embodiment. Thus, for example, a given embodiment may include only a second mirror and a third traversal.

Additional Embodiments

The disclosure also includes the following numbered embodiments:

1. An optical coherence tomography (OCT) system for scanning an anatomical item, the system comprising:
   - a scanning device, which is moveable by a user relative to the anatomical item to scan the anatomical item, the scanning device comprising:
   - a beam steering system, which is operable to deflect a sample beam by respective, selected amounts in two directions;
   - one or more optical elements, which direct the sample beam through an imaging window of the scanning device to an exterior of the scanning device, and which receive light returned from the anatomical item through the imaging window and direct said returned light to an interferometry system of the OCT system, wherein the interferometry system is configured to cause interference between the returned light and light from a light source that produces the sample beam, and to analyze said interference; and
   - a camera, operable to capture visible light images of a region exterior the scanning device, adjacent the imaging window, each of said images comprising a plurality of pixels, the camera having an optical axis that defines an acute angle with respect to a central axis for the sample beam, following emission through the imaging window;
   - at least one processor; and
   - data storage, on which is stored instructions that, when executed by the at least one processor, cause the OCT system to perform actions comprising:
     - controlling the beam steering system such that the sample beam, after exiting the imaging window, repeatedly traverses a two-dimensional scanning pattern, with the movement of the scanning device by the user relative to the anatomical item causing the repeated traversals of the scanning pattern to be applied to respective, different locations on the anatomical item;
   - for each traversal of the scanning pattern, carrying out a plurality of A-scans at respective points distributed over the scanning pattern, so as to generate a set of volumetric OCT scanning data, said repeated traversals of the scanning pattern thereby generating a plurality of sets of volumetric OCT scanning data;
   - during said repeated traversals of the scanning pattern, controlling the camera to repeatedly capture visible light images of the anatomical item;
   - for each set of volumetric OCT scanning data:
     - identifying a plurality of points on an exterior surface of the anatomical item, each of the plurality of points corresponding to one the plurality of A-scans used to generate the set of volumetric OCT scanning data;
     - determining an association between each of said plurality of points and a respective subset of pixels of an image captured by the camera at a time corresponding to the volumetric OCT scanning data; and
     - determining spacings between the subsets of pixels corresponding to the plurality of points;
     - based on said spacings, identifying, within the subsets of pixels, groups of potentially mutually obscuring subsets of pixels, each group of potentially mutually obscuring subsets of pixels corresponding to a group of potentially mutually obscuring exterior surface points among the plurality of points; and
   - generating a 3D model of the anatomical item, using the plurality of sets of volumetric OCT scanning data, wherein the generating of the 3D model comprises:
     - for each set of volumetric OCT scanning data, adding a plurality of exterior surface portions, each of which is based on at least one of the plurality of points on the exterior surface of the anatomical item identified using the set of volumetric OCT scanning data; and
     - determining coloring parameters for the plurality of exterior surface portions, based on said association between each of said plurality of points and the respective subset of pixels of said image captured by the camera,
     - wherein, for a given exterior surface portion that is based on a given point of a group of potentially mutually obscuring points, the determining of the color parameters is further based on a proximity of the given point to the camera, relative to the proximity to the camera of each of the other potentially mutually obscuring exterior surface points in the group.

2. The system of embodiment 1, wherein, for said given exterior surface portion based on the given point of the group of potentially mutually obscuring points, the determining of the color parameters comprises determining whether the given point is closer to the camera than all other potentially mutually obscuring exterior surface points in the group, and, only if so, the determining of the color parameters of the given exterior surface portion is based on the subset of pixels corresponding to the given point.

3. The system of embodiment 2, wherein, if the given point is not closer to the camera than all other potentially mutually obscuring exterior surface points in the group, the determining of the color parameters of the given exterior surface portion is based on at least one predetermined contrast color.

4. The system of any preceding embodiment, wherein said identifying, within the subsets of pixels, groups of potentially mutually obscuring subsets of pixels, is further based on respective distances from the camera of the points corresponding to the subsets of pixels.

5. The system of any preceding embodiment, wherein the scanning device is a handheld device.

6. An optical coherence tomography (OCT) system for scanning an anatomical item, the system comprising:

a scanning device, which is moveable by a user relative to the anatomical item to scan the anatomical item, the scanning device comprising:

a beam steering system, which is operable to deflect a sample beam by respective, selected amounts in two directions;

one or more optical elements, which direct the sample beam through an imaging window of the scanning device to an exterior of the scanning device, and which receive light returned from the anatomical item through the imaging window and direct said returned light to an interferometry system of the OCT system, wherein the interferometry system is configured to cause interference between the returned light and light from a light source that produces the sample beam, and to analyze said interference; and a camera, operable to capture visible light images of a region exterior the scanning device, adjacent the imaging window, wherein the camera and the window are disposed at a distal end of the scanning device, with an optical axis of the camera being oriented towards said region exterior the scanning device;

at least one processor; and data storage, on which is stored instructions that, when executed by the at least one processor, cause the OCT system to perform actions comprising:

controlling the beam steering system such that the sample beam, after exiting the imaging window, repeatedly traverses a two-dimensional scanning pattern, with the movement of the scanning device by the user relative to the anatomical item causing the repeated traversals of the scanning pattern to be applied to respective, different locations on the anatomical item;

for each traversal of the scanning pattern, carrying out a plurality of A-scans at respective points distributed over the scanning pattern, so as to generate a set of volumetric OCT scanning data, said repeated traversals of the scanning pattern thereby generating a plurality of sets of volumetric OCT scanning data;

during said repeated traversals of the scanning pattern, controlling the camera to repeatedly capture visible light images of the anatomical item;

for each set of volumetric OCT scanning data:

identifying a plurality of points on an exterior surface of the anatomical item, each of the plurality of points corresponding to one the plurality of A-scans used to generate the set of volumetric OCT scanning data; and determining an association between said plurality of points and pixels of an image captured by the camera at a time corresponding to the volumetric OCT scanning data; and generating a 3D model of the anatomical item, using the plurality of sets of volumetric OCT scanning data, wherein the generating of the 3D model comprises:

for each set of volumetric OCT scanning data, adding a plurality of exterior surface portions, based on the plurality of points on the exterior surface of the anatomical item identified using the set of volumetric OCT scanning data; and determining coloring parameters for the plurality of exterior surface portions, based on said pixels of the image captured by the camera at the time corresponding to the volumetric OCT scanning data.

7. The system of claim 6, wherein, for each set of volumetric OCT scanning data, each of the plurality of points on the exterior surface of the anatomical item corresponds to one the plurality of A-scans used to generate the set of volumetric OCT scanning data, wherein, for each set of volumetric OCT scanning data, determining the association between said plurality of points and said pixels of the image captured by the camera at the time corresponding to the volumetric OCT scanning data comprises determining an association between each of said plurality of points and a respective subset of the pixels of the image captured by the camera at the time corresponding to the volumetric OCT scanning data, wherein, for each set of volumetric OCT scanning data, each of the corresponding exterior surface portions is based on at least one of the plurality of points on the exterior surface of the anatomical item identified using the set of volumetric OCT scanning data, and wherein the determining of the coloring parameters for the plurality of exterior surface portions is based on said association between each of said plurality of points and the respective subset of pixels of said image captured by the camera.

8. The system of embodiment 6 or embodiment 7, wherein the optical axis of the camera extends through the window.

9. The system of any one of embodiments 6-8, wherein the camera and the window are disposed on a first lateral side of the scanning device.

10. The system of any one of embodiments 6-9, wherein the window is disposed on a first lateral side of the scanning device and the camera is disposed on an opposing, second lateral side of the scanning device.

11. The system of embodiment 10, wherein the one or more optical elements comprise a distal mirror, which directs the sample beam in a direction generally perpendicular to a length of the scanning device, through the window, and wherein the camera is disposed proximally of the distal mirror.

12. The system of any one of embodiments 6-11, wherein the scanning device is a handheld device.

What is claimed is:

1. An optical coherence tomography (OCT) system for scanning an anatomical item, the system comprising:

a scanning device, which is moveable by a user relative to the anatomical item to scan the anatomical item, the scanning device comprising:

a beam steering system, which is operable to deflect a sample beam by respective, selected amounts in two directions;

one or more optical elements, which direct the sample beam through an imaging window of the scanning device to an exterior of the scanning device, and which receive light returned from the anatomical item through the imaging window and direct said returned light to an interferometry system of the OCT system, wherein the interferometry system is configured to cause interference between the returned light and light from a light source that produces the sample beam, and to analyze said interference; and a camera, operable to capture visible light images of a region exterior the scanning device and adjacent the imaging window, each of said images comprising a plurality of pixels, wherein the camera and the imaging window are disposed at a distal end of the scanning device, with an optical axis of the camera being oriented towards said region exterior the scanning device;

at least one processor; and data storage, on which is stored instructions that, when executed by the at least one processor, cause the OCT system to perform actions comprising:

controlling the beam steering system such that the sample beam, after exiting the imaging window, repeatedly traverses a two-dimensional scanning pattern, with the movement of the scanning device by the user relative to the anatomical item causing the repeated traversals of the two-dimensional scanning pattern to be applied to respective, different locations on the anatomical item;

for each traversal of the two-dimensional scanning pattern, carrying out a plurality of A-scans at respective points distributed over the two-dimensional scanning pattern, so as to generate a set of volumetric OCT scanning data, said repeated traversals of the two-dimensional scanning pattern thereby generating a plurality of sets of volumetric OCT scanning data;

during said repeated traversals of the two-dimensional scanning pattern, controlling the camera to repeatedly capture visible light images of the anatomical item;

for each set of volumetric OCT scanning data:

identifying a plurality of points on an exterior surface of the anatomical item, each of the plurality of points corresponding to one of the plurality of A-scans used to generate the set of volumetric OCT scanning data;

determining an association between each of said plurality of points and a respective subset of pixels of an image captured by the camera at a time corresponding to the set of volumetric OCT scanning data; and determining spacings between the subsets of pixels corresponding to the plurality of points;

based on said spacings, identifying, within the subsets of pixels, groups of potentially mutually obscuring subsets of pixels, each group of potentially mutually obscuring subsets of pixels corresponding to a group of potentially mutually obscuring exterior surface points among the plurality of points; and generating a 3D model of the anatomical item, using the plurality of sets of volumetric OCT scanning data, wherein the generating of the 3D model comprises:

for each set of volumetric OCT scanning data, adding a plurality of exterior surface portions, each of which is based on at least one of the plurality of points on the exterior surface of the anatomical item identified using the set of volumetric OCT scanning data; and determining coloring parameters for the plurality of exterior surface portions, based on said association between each of said plurality of points and the respective subset of pixels of said image captured by the camera, wherein, for a given exterior surface portion that is based on a given point of a group of potentially mutually obscuring points, the determining of the color parameters is further based on a proximity of the given point to the camera, relative to the proximity to the camera of each of the other potentially mutually obscuring exterior surface points in the group.

2. The system of claim 1, wherein, for said given exterior surface portion based on the given point of the group of potentially mutually obscuring points, the determining of the color parameters comprises determining whether the given point is closer to the camera than all other potentially mutually obscuring exterior surface points in the group, and, only if so, the determining of the color parameters of the given exterior surface portion is based on the subset of pixels corresponding to the given point.

3. The system of claim 2, wherein, if the given point is not closer to the camera than all other potentially mutually obscuring exterior surface points in the group, the determining of the color parameters of the given exterior surface portion is based on at least one predetermined contrast color.

4. The system of claim 1, wherein said identifying, within the subsets of pixels, groups of potentially mutually obscuring subsets of pixels, is further based on respective distances from the camera of the points corresponding to the subsets of pixels.

5. The system of claim 1, wherein the scanning device is a handheld device.

6. The system of claim 1, wherein the optical axis of the camera extends through the imaging window.

7. The system of claim 1, wherein the camera and the imaging window are disposed on a first lateral side of the scanning device.

8. The system of claim 1, wherein the imaging window is disposed on a first lateral side of the scanning device and the camera is disposed on an opposing, second lateral side of the scanning device.

9. The system of claim 8, wherein the one or more optical elements comprise a distal mirror, which directs the sample beam in a direction generally perpendicular to a length of the scanning device, through the imaging window, and wherein the camera is disposed proximally of the distal mirror.

* * * * *